(12) United States Patent
Abbitt et al.

(10) Patent No.: US 12,371,702 B2
(45) Date of Patent: Jul. 29, 2025

(54) IMPROVING AGRONOMIC CHARACTERISTICS IN MAIZE BY MODIFICATION OF ENDOGENOUS MADS BOX TRANSCRIPTION FACTORS

(71) Applicant: PIONEER HI-BRED INTERNATIONAL, INC., Johnston, IA (US)

(72) Inventors: Shane E Abbitt, Ankeny, IA (US); Mary J Frank, Des Moines, IA (US); Shai Lawit, Urbandale, IA (US); Rosana Melo, St Charles, MO (US); Mary A Rupe, Altoona, IA (US); Bo Shen, Johnston, IA (US); Jingrui Wu, Johnston, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 11 days.

(21) Appl. No.: 17/047,946

(22) PCT Filed: Apr. 16, 2019

(86) PCT No.: PCT/US2019/027602
§ 371 (c)(1),
(2) Date: Oct. 15, 2020

(87) PCT Pub. No.: WO2019/204256
PCT Pub. Date: Oct. 24, 2019

(65) Prior Publication Data
US 2021/0155949 A1 May 27, 2021

Related U.S. Application Data

(60) Provisional application No. 62/814,373, filed on Mar. 6, 2019, provisional application No. 62/741,529, filed on Oct. 4, 2018, provisional application No. 62/659,579, filed on Apr. 18, 2018.

(51) Int. Cl.
*C12N 15/82* (2006.01)
*A01H 5/10* (2018.01)

(52) U.S. Cl.
CPC .......... *C12N 15/8241* (2013.01); *A01H 5/10* (2013.01)

(58) Field of Classification Search
None
See application file for complete search history.

(56) References Cited

U.S. PATENT DOCUMENTS

| | | |
|---|---|---|
| 5,510,474 A | 4/1996 | Quail et al. |
| 5,811,536 A | 9/1998 | Yanofsky |
| 5,859,326 A | 1/1999 | An |
| 5,981,840 A | 11/1999 | Zhao et al. |
| 5,990,386 A | 11/1999 | An |
| 6,025,483 A | 2/2000 | Yanofsky |
| 6,025,543 A | 2/2000 | Yanofsky |
| 6,229,068 B1 | 5/2001 | Yanofsky et al. |
| 6,504,083 B1 | 1/2003 | Barbour et al. |
| 6,995,302 B1 | 2/2006 | Kojima et al. |
| 11,124,801 B2 | 9/2021 | Coles et al. |
| 11,421,242 B2 | 8/2022 | Christensen et al. |
| 2002/0129403 A1 | 9/2002 | Yanofsky et al. |
| 2004/0019933 A1 | 1/2004 | Podila et al. |
| 2004/0241651 A1 | 12/2004 | Olek et al. |
| 2005/0091717 A1 | 4/2005 | Amasino et al. |
| 2005/0108791 A1 | 5/2005 | Edgerton |
| 2005/0241014 A1 | 10/2005 | Colliver et al. |
| 2006/0206965 A1 | 9/2006 | Gleissner et al. |
| 2006/0236419 A1 | 10/2006 | La Rosa et al. |
| 2006/0248612 A1 | 11/2006 | Vancanneyt et al. |
| 2007/0006344 A1 | 1/2007 | Nuccio et al. |
| 2007/0033671 A1 | 2/2007 | Jiang et al. |
| 2007/0039070 A1 | 2/2007 | Bloksberg et al. |
| 2007/0048756 A1 | 3/2007 | Mei et al. |
| 2007/0136891 A1* | 6/2007 | Niu .................. C12N 15/823 800/320.2 |

(Continued)

FOREIGN PATENT DOCUMENTS

| | | |
|---|---|---|
| CN | 101629184 A | 1/2010 |
| CN | 102002101 A | 4/2011 |

(Continued)

OTHER PUBLICATIONS

Sun, Engineering Herbicide-Resistant Rice Plants through CRIPSR/Cas9-Mediated Homologous Recombination of Acetolactate Synthase, Cell, Jan. 5, 2016 (Year: 2016).*
Schmitz, Robert J., Erich Grotewold, and Maike Stam. "Cis-regulatory sequences in plants: Their importance, discovery, and future challenges." The Plant Cell 34.2 (2022): 718-741 (Year: 2022).*
Meyer, The Future of Food? CRISPR-Edited Agriculture, Food and Drug Law Institute, Nov. 2021 (Year: 2021).*
Zhang, Zhongbao, et al. "Characterization and expression analysis of six MADS-box genes in maize (Zea mays L.)." Journal of plant physiology 169.8 (2012): 797-806. (Year: 2012).*

(Continued)

*Primary Examiner* — Weihua Fan
*Assistant Examiner* — Brian James Sullivan

(57) ABSTRACT

Genome edited plants, plant cells, seeds and plant parts of maize are provided where expression levels and/or activities of MADS-box transcription factors are modulated to improve one or more agronomic characteristics such as grain yield. Also provided are compositions comprising polynucleotides encoding polypeptides and guide RNAs targeted to endogenous maize MADS-box proteins including for example, targeted site-directed mutagenesis using CRISPR-associated nucleases. Additionally, various methods of employing the polynucleotides and genetic modifications in plants, such as methods for modulating expression level in a maize plant and methods for increasing yield of a maize plant are also provided herein.

10 Claims, 6 Drawing Sheets
Specification includes a Sequence Listing.

(56) References Cited

U.S. PATENT DOCUMENTS

| | | |
|---|---|---|
| 2007/0250945 A1 | 10/2007 | Sung et al. |
| 2007/0270578 A1 | 11/2007 | Frankard |
| 2009/0089896 A1 | 4/2009 | Wiig et al. |
| 2009/0100536 A1 | 4/2009 | Adams et al. |
| 2009/0217406 A1 | 8/2009 | Puzio et al. |
| 2009/0255013 A1 | 10/2009 | Alvarez-Venegas et al. |
| 2010/0017546 A1 | 1/2010 | Poo et al. |
| 2010/0024065 A1 | 1/2010 | Mullet et al. |
| 2010/0175146 A1* | 7/2010 | Bruce .................. C07K 14/415 536/23.6 |
| 2010/0186114 A1 | 7/2010 | Spangenberg et al. |
| 2010/0218273 A1 | 8/2010 | Bruce |
| 2010/0257637 A1 | 10/2010 | Shirley et al. |
| 2011/0093985 A1 | 4/2011 | Suzuki et al. |
| 2011/0178283 A1 | 7/2011 | Rigoutsos et al. |
| 2012/0042411 A1 | 2/2012 | Malcuit et al. |
| 2012/0227131 A1 | 9/2012 | Abad et al. |
| 2013/0019342 A1 | 1/2013 | Duncan et al. |
| 2013/0074202 A1 | 3/2013 | Adams et al. |
| 2013/0263324 A1 | 10/2013 | Lassner et al. |
| 2014/0130202 A1 | 5/2014 | Gantet et al. |
| 2015/0064759 A1 | 3/2015 | Perez et al. |
| 2015/0128309 A1 | 5/2015 | Sastry-Dent et al. |
| 2015/0240253 A1 | 8/2015 | Mcgonigle et al. |
| 2015/0284737 A1 | 10/2015 | Bate et al. |
| 2015/0322452 A1 | 11/2015 | Wang et al. |
| 2016/0138036 A1 | 5/2016 | Park et al. |
| 2016/0168586 A1 | 6/2016 | Beazley et al. |
| 2016/0237447 A1 | 8/2016 | Abad et al. |
| 2016/0304890 A1 | 10/2016 | Song et al. |
| 2017/0114356 A1 | 4/2017 | Li et al. |
| 2017/0114359 A1 | 4/2017 | Bohannon et al. |
| 2017/0240915 A1 | 8/2017 | Zhou et al. |
| 2021/0155951 A1 | 5/2021 | La Rota et al. |
| 2021/0171971 A1 | 6/2021 | Haug Collet et al. |
| 2021/0388370 A1 | 12/2021 | Coles et al. |
| 2022/0378000 A1 | 12/2022 | Habben et al. |
| 2022/0380794 A1 | 12/2022 | Christensen et al. |

FOREIGN PATENT DOCUMENTS

| | | |
|---|---|---|
| WO | WO-9400582 A2 | 1/1994 |
| WO | WO-9746078 A1 | 12/1997 |
| WO | WO-9904003 A1 | 1/1999 |
| WO | WO-9947654 A2 | 9/1999 |
| WO | WO-0032780 A1 | 6/2000 |
| WO | WO-0037488 A2 | 6/2000 |
| WO | WO-0119995 A1 | 3/2001 |
| WO | WO-0229028 A2 | 4/2002 |
| WO | WO-0233091 A1 | 4/2002 |
| WO | WO-2004035797 A2 | 4/2004 |
| WO | 2006032707 A2 | 3/2006 |
| WO | WO-2007106593 A2 | 9/2007 |
| WO | WO-2007110600 A2 | 10/2007 |
| WO | WO-2007132789 A1 | 11/2007 |
| WO | 2008148872 A1 | 12/2008 |
| WO | WO-2011022469 A2 | 2/2011 |
| WO | WO-2011062904 A1 | 5/2011 |
| WO | 2011140329 A1 | 11/2011 |
| WO | WO-2012129373 A2 | 9/2012 |
| WO | WO-2013025400 A1 | 2/2013 |
| WO | WO-2013066805 A1 | 5/2013 |
| WO | WO-2014143996 A2 | 9/2014 |
| WO | WO-2014208508 A1 | 12/2014 |
| WO | 2016134081 A1 | 8/2016 |
| WO | WO-2017106663 A1 | 6/2017 |

OTHER PUBLICATIONS

Zhang, Zhongbao. "MADS-Domain Transcription Factor [*Zea mays*]—Protein—NCBI." National Center for Biotechnology Information, U.S. National Library of Medicine, Sep. 21, 2012, Accessed Dec. 10, 2024. (Year: 2012).*

Shi, Jinrui, et al. "ARGOS 8 variants generated by CRISPR-Cas9 improve maize grain yield under field drought stress conditions." Plant biotechnology journal 15.2 (2017): 207-216. (Year: 2017).*

International Search Report and Written Opinion for International Application PCT/US19/27602, Mailed Sep. 3, 2019.

Extended European Search Report for European Application 19789170.8 Mailed Feb. 3, 2022.

Riechmann J L et al: "MADS Domain Proteins in Plant Development", Biological Chemistry, Walter De Gruyter GMBH & Co, Berlin, DE, vol. 378, Oct. 1, 1997 (Oct. 1, 1997).

Chen et al., (2013) A Novel Moderate Constitutive Promoter Derived from Poplar (*Populus tomentosa* Carrière), Int J Mol Sci. Mar. 18, 2013; 14(3): 6187-6204.

An G., et al., "Functional Analysis of the 3' Control Region of the Potato Wound-Inducible Proteinase Inhibitor II Gene," The Plant Cell, Jan. 1989, vol. 1, pp. 115-122.

Anderson J. A., et al., "Hypothesis-based Food, Feed, and Environmental Safety Assessment of GM crops: A Case Study using Maize Event DP-202216-6," Biotechnology in Agriculture and the Food Chain, 2021, vol. 12, No. 1, pp. 282-291.

Andorf C.M., et al., "MaizeGDB Update: New Tools, Data and Interface for the Maize Model Organism Database," Nucleic Acids Research, 2016, vol. 44, pp. D1195-D1201.

Ashburner M., et al., "Gene Ontology: Tool for the Unification of Biology," Nature Genetics, May 2000, vol. 25, No. 1, pp. 25-29, 09 pages.

Assem S.K., et al., "Comparison of the Efficiency of Some Novel Maize Promoters in Monocot and Dicot Plants," Arab Journal of Biotechnology, Jan. 2002, vol. 5, No. 1, pp. 57-66.

Baowen H., et al., "Overexpression of the Class D MADS-Box Gene SL-AGL11 Impacts Fleshy Tissue Differentiation and Structure in Tomato Fruits," Journal of Experimental Botany, 2017, vol. 68, No. 17, pp. 4869-4884.

Becker A., et al., "The Major Clades of MADS-Box Genes and their Role in the Development and Evolution of Flowering Plants," Molecular Phylogenetics and Evolution, Apr. 2003, vol. 29, pp. 464-489.

Bricker T.M., et al., "The PsbP Family of Proteins," Photosynthesis Research, 2013, vol. 116, pp. 235-250.

Castiglioni P., et al., "Bacterial RNA Chaperones Confer Abiotic Stress Tolerance in Plants and Improved Grain Yield in Maize Under Water-Limited Conditions," Plant Physiology, Jun. 2008, vol. 147, pp. 446-455.

Catron S.A., et al., "Petition for Determination of Nonregulated Status for Enhanced Grain Yield Potential and Glufosinate-Ammonium Resistant DP202216 Maize," USDA-APHIS, Jun. 3, 2019, 230 Pages.

Century K., et al., "Regulating the Regulators: The Future Prospects for Transcription-Factor-Based Agricultural Biotechnology Products," Plant Physiology, May 2008, vol. 147, pp. 20-29.

Christensen A.H., et al., "Maize Polyubiquitin Genes: Structure, Thermal Perturbation of Expression and Transcript Splicing, and Promoter Activity Following Transfer to Protoplasts by Electroporation," Plant Molecular Biology, 1992, vol. 18, pp. 675-689.

Coen E.S., et al., "The War of the Whorls: Genetic Interactions Controlling Flower Development," Nature, Sep. 5, 1991, vol. 353, pp. 31-37.

De Pater B.S., et al., "The Promoter of the Rice Gene GOS2 is Active in Various Different Monocot Tissues and Binds Rice Nuclear Factor ASF-I," The Plant Journal, 1992, vol. 2, No. 6, pp. 837-844.

De Veau E.J., et al., "Photorespiratory Rates in Wheat and Maize as Determined by O-Labeling," Plant Physiology, 1989, vol. 90, pp. 500-511.

Du Z., et al., "AgriGO: a GO Analysis Toolkit for the Agricultural Community," Nucleic Acids Research, 2010, vol. 38, pp. W64-W70, Published online on Apr. 30, 2010.

Echarte L., et al., "Kernel Number Determination in Argentinean Maize Hybrids Released between 1965 and 1993," Drop Science, 2004, vol. 44, pp. 1654-1661.

Egli D.B., et al., "Is There a Role for Sink Size in Understanding Maize Population-Yield Relationships?," Crop Science, Nov.-Dec. 2015, vol. 55, pp. 2453-2462.

(56) References Cited

OTHER PUBLICATIONS

Extended European Search Report for European Application No. 19787744.2 mailed Dec. 3, 2021, 09 Pages.
Ferrandiz C., et al., "Redundant Regulation of Meristem Identity and Plant Architecture by Fruitfull, APETALA1 and Cauliflower," Development, 2000, vol. 127, pp. 725-734.
Fornara F., et al., "Functional Characterization of OsMADS18, a Member of the AP1/SQUA Subfamily of MADS Box Genes," Plant Physiology, Aug. 2004, vol. 135, pp. 2207-2219.
Gan Y., et al: "Nutritional Regulation of ANR1 and Other Root-Expressed MADS-Box Genes in *Arabidopsis thaliana*," Planta, 2005, vol. 222, pp. 730-742.
Gilmore A.R., et al., "ASReml User Guide," Release 3.0, 2009, NSW Department of Industry and Investment; HP1 IES, pp. 1-372, 399 Pages.
Gilmour A.R., et al., "Average Information REML: An Efficient Algorithm for Variance Parameter Estimation in Linear Mixed Models," Biometrics, Dec. 1995, vol. 51, No. 4, pp. 1440-1450.
Gramzow L., et al., "A Hitchhikers Guide to the MADS world of plants," Genome Biology, Jun. 28, 2010, vol. 11, pp. 1-11.
Guo H.H., et al., "Protein Tolerance to Random Amino Acid Change," Proceedings of National Academy of Sciences, USA, Jun. 22, 2004, vol. 101, No. 25, pp. 9205-9210.
Guo S., et al., "The Interaction Between OsMADS57 and OsTB1 Modulates Rice Tillering via DWARF14," Nature Communications, Mar. 5, 2013, vol. 4, pp. 1-12.
Habben J.E., et al., "Transgenic Alteration of Ethylene Biosynthesis Increases Grain Yield in Maize Under Field Drought-Stress Conditions," Plant Biotechnology Journal, 2014, vol. 12, pp. 685-693.
Hanma Z., et al., "An *Arabidopsis* MADS Box Gene That Controls Nutrient-Induced Changes in Root Architecture," Science, Jan. 16, 1998, vol. 279, pp. 407-409, 4 Pages.
Hartmann U., et al., "Molecular Cloning of Svp: A Negative Regulator of the Floral Transition in Arabidopsis," The Plant Journal, 2000, vol. 21, No. 4, pp. 351-360.
Hensgens L.A.M., et al., "Transient and Stable Expression of gusA Fusions with Rice Genes in Rice, Barley and Perennial Ryegrass," Plant Molecular Biology, 1993, vol. 23, pp. 643-669.
Hoagland D.R., et al., "The Water-Culture Method for Growing Plants without Soil," California Agricultural Experiment Station, 1950, vol. 347, pp. 1-32.
Horstman A., et al., "A Cautionary Note on the use of Split-YFP/BiFC in Plant Protein-Protein Interaction Studies," International Journal of Molecular Sciences, May 30, 2014, vol. 15, pp. 9628-9643.
Huang H., et al., "DNA Binding Properties of Two *Arabidopsis* MADS Domain Proteins: Binding Consensus and Dimer Formation," The Plant Cell, Jan. 1996, vol. 8, pp. 81-94.
International Preliminary Report on Patentability for International Application No. PCT/US2019/027599, mailed Oct. 29, 2020, 14 Pages.
International Preliminary Report on Patentability for International Application No. PCT/US2019/027602, mailed Oct. 29, 2020, 9 Pages.
International Preliminary Report on Patentability for International Application No. PCT/US2019/027617, mailed Oct. 29, 2020, 11 Pages.
International Preliminary Report on Patentability for International Application No. PCT/US2019/027782, mailed Oct. 29, 2020, 10 Pages.
International Search Report and Written Opinion for International Application No. PCT/US2019/027599, mailed Sep. 16, 2019, 19 Pages.
International Search Report and Written Opinion for International Application No. PCT/US2019/027617, mailed Sep. 16, 2019, 16 Pages.
International Search Report and Written Opinion for International Application No. PCT/US2019/027782, mailed Sep. 3, 2019, 18 Pages.
Jiao Y., et al., "Improved Maize Reference Genome with Single-Molecule Technologies," Nature, Jun. 22, 2017, vol. 546, pp. 524-539, 16 pages.
Kanai R., et al., "Separation of Mesophyll Protoplasts and Bundle Sheath Cells from Maize Leaves for Photosynthetic Studies," Plant Physiology, 1973, vol. 51, pp. 1133-1137.
Kim S-I., et al., "Genome-Wide Analysis of Agrobacterium T-DNA Integration Sites in the *Arabidopsis* Genome Generated Under Non-Selective Conditions," The Plant Journal, Sep. 2007, Epub Jun. 30, 2007 year: 2007, vol. 51, No. 5, pp. 779-791.
Krall J.P., et al., "Protection of Pyruvate, Pi Dikinase from Maize Against Cold Lability by Compatible Solutes," Plant Physiology, 1989, vol. 89, pp. 280-285.
Kyte J., et al., "A Simple Method for Displaying the Hydropathic Character of a Protein," Journal of Molecular Biology, 1982, vol. 157, No. 1, pp. 105-132.
Langmead B., et al., "Ultrafast and Memory-Efficient Alignment of Short DNA Sequences to the Human Genome," Genome Biology, 2009, vol. 10, Issue 3, Article R25, pp. 1-10.
Lawit S.J., et al., "Maize DELLA Proteins Dwarf Plant8 and Dwarf Plant9 as Modulators of Plant Development," Plant Cell Physiology, 2010, vol. 51, No. 11, pp. 1854-1868.
Lawit S.J., et al., "Transgenic Manipulation of Plant Embryo Sacs Tracked Through Cell-type-specific Fluorescent Markers: Cell labeling, Cell ablation, and Adventitious Embryos," Plant Reproduction, 2013, vol. 26, pp. 125-137.
Li B., et al., "RSEM: accurate Transcript Quantification from RNA-Seq Data With or Without a Reference Genome," BMC Bioinformatics, 2011, vol. 12, No. 323, pp. 1-16.
Li Q., et al., "Measuring Reproducibility of High-Throughput Experiments," The Annals of Applied Statistics, Oct. 2011, vol. 5, No. 3, pp. 1752-1779, 29 pages.
LOC100281199 Gene Summary from NCBI.txt Downloaded from the NCBI website, May 18, 2023, Retrieved from URL: https://www.ncbi.nlm.nih.gov/.
Love M.I., et al., "Moderated Estimation of Fold Change and Dispersion for RNA-seq Data with DESeq2," Genome Biology, 2014, vol. 15, No. 550, pp. 1-21.
"MADS-box transcription factor 18 [*Zea mays*],"NCBI Reference Sequence: NP_001105155.1, 2014, 2 pages.
Mandel M.A., et al., "The *Arabidopsis* AGL8 Mads Box Gene is Expressed in Inflorescence Meristems and is Negatively Regulated by APETALA1," The Plant Cell, Nov. 1995, vol. 7, pp. 1763-1771.
Masclaux-Daubresse C., et al., "Nitrogen Uptake, Assimilation and Remobilization in Plants: Challenges for Sustainable and Productive Agriculture, " Annals of Botany, 2010, vol. 105, pp. 1141-1157.
Matias-Hernandez L., et al., "VERDANDI is a Direct Target of the MADS Domain Ovule Identity Complex and Affects Embryo Sac Differentiation in *Arabidopsis*," The Plant Cell, Jun. 2010, vol. 22, pp. 1702-1715.
Maxwell K., et al., "Chlorophyll fluorescence—A Practical Guide," Journal of Experimental Botany, Apr. 2000, vol. 51, No. 345, pp. 659-668.
Munster T., et al., "Maize MADS-Box Genes Galore," Maydica, 2002, vol. 47, pp. 287-301.
Nelson D.E., et al., "Plant Nuclear Factor Y (NF-Y) B Subunits Confer Drought Tolerance and Lead to Improved Corn Yields on Water-limited Acres," Proceedings of the National Academy of Sciences of the United States of America, Oct. 16, 2007, vol. 104, No. 42, pp. 16450-16455.
Nuccio M.L., et al., "Expression of Trehalose-6-Phosphate Phosphatase in Maize Ears Improves Yield in Well-Watered and Drought Conditions," Nature Biotechnology, Aug. 2015, vol. 33, No. 8, pp. 862-869, 13 Pages.
Office Action for Canadian Application No. 3,094,027 (PCT No. US2019027599), mailed Dec. 14, 2021, 4 pages.
Olsen A.N., et al., "NAC Transcription Factors: Structurally Distinct, Functionally Diverse," Trends in Plant Science, Feb. 2005, vol. 10, No. 2, Feb. 2005, pp. 79-87.
Onouchi H., et al., "Mutagenesis of Plants Overexpressing CONSTANS Demonstrates Novel Interactions among *Arabidopsis* Flowering-Time Genes," The Plant Cell, Jun. 2000, vol. 12, pp. 885-900.

(56) References Cited

OTHER PUBLICATIONS

Ort D.R., et al., "Redesigning Photosynthesis to Sustainably Meet Global Food and Bioenergy Demand," PNAS, Jul. 14, 2015, vol. 112, No. 28, pp. 8529-8536.
Perez-Rodriguez P., et al., "PlnTFDB: Updated Content and New Features of the Plant Transcription Factor Database," Nucleic Acids Research, 2010, Oct. 25, 2009, vol. 38, pp. D822-D827.
Predicted: Sorghum bicolor MADS-box transcription factor 18 (LOC8079022), GenBank accession No. XM_002460944.2, 2017.
Purugganan M.D., et al., "Molecular Evolution of Flower Development: Diversification of the Plant MADS-Box Regulatory Gene Family," Genetics Society of America, May 1995, vol. 140; pp. 345-356.
Rabara R.C., et al., "The Potential of Transcription Factor-Based Genetic Engineering in Improving Crop Tolerance to Drought," Omics A Journal of Integrative Biology, 2014, vol. 18, No. 10, pp. 601-614.
Ray D.K., et al., "Yield Trends Insufficient to Double Global Crop Production by 2050," PLoS ONE, Jun. 19, 2013, vol. 8, No. 6, pp. 1-2.
Rice E.A., et al., "Expression of a Truncated ATHB17 Protein in Maize Increases Ear Weight at Silking," PLOS ONE, Apr. 15, 2014, vol. 9, No. 4(e94238), pp. 1-21.
Sachdeva R., GenBank LR756505.1 (3020).
Schilling S., et al., "MADS-Box Genes and Crop Domestication: the Jack of all Traits," Journal of Experimental Botany; Published on Feb. 21, 2018, vol. 69, No. 7, pp. 1447-1469.
Schwarz-Sommer Z., et al., "Genetic Control of Flower Development by Homeotic Genes in Antirrhinum Majus," Articles, Science, Nov. 16, 1990, vol. 250, pp. 931-936.
Shcherbo D., et al., "Far-Red Fluorescent Tags for Protein Imaging in Living Tissues," Biochemical Journal, Mar. 15, 2009, vol. 418, No. 3, pp. 567-574, 14 pages.
Shi J., et al., "Overexpression of ARGOS Genes Modifies Plant Sensitivity to Ethylene, Leading to Improved Drought Tolerance in Both Arabidopsis and Maize [Open]," Plant Physiology, Sep. 2015, vol. 169, pp. 266-282.
Shore P., et al., "The MADS-Box Family of Transcription Factors," European Journal of Biochemistry, FEBS, 1995, vol. 229, pp. 1-13.
Song G.Q., et al., "Overexpression of the MADS-Box Gene K-domain Increases the Yield potential of Blueberry," Plant Science, 2018, vol. 276, pp. 22-31.
Song Q.X., et al., "Soybean GmbZIP123 Gene Enhances Lipid Content in the Seeds of Transgenic Arabidopsis Plants," Journal of Experimental Botany, 2013, vol. 64, No. 14, pp. 4329-4341.
Sun J., et al., "Inconsistency of Mesophyll Conductance Estimate Causes the Inconsistency for the Estimates of Maximum Rate of Rubisco Carboxylation among the Linear, Rectangular and Non-Rectangular Hyperbola Biochemical Models of Leaf Photosynthesis—A Case Study of CO2 Enrichment and Leaf Aging Effects in Soybean," Plant Science, 2014, vol. 226, pp. 49-60.
Sun J., et al., "Interactions of Nitrate and CO2 Enrichment on Growth, Carbohydrates, and Rubisco in *Arabidopsis* Starch Mutants. Significance of Starch and Hexose1," Plant Physiology, Nov. 2002, vol. 130, pp. 1573-1583.
Tang W., et al., "Binding Site Selection for the Plant MADS Domain Protein AGL15," An In Vitro and In Vivo Study, The Journal of Biological Chemistry, May 12, 2003, vol. 278, No. 30, pp. 28154-28159, 7 Pages, Jul. 25, 2003.
Theissen G., et al., "Floral quartets," Nature, Jan. 25, 2001, vol. 409, pp. 469-471.

Thompson J.D., et al., "The CLUSTAL_X Windows Interface: Flexible Strategies for Multiple Sequence Alignment Aided by Quality Analysis Tools, " Nucleic Acids Research, 1997, vol. 25, No. 24, pp. 4876-4882.
Trachsel S., et al., "Interrelations among Early Vigor, Flowering Time, Physiological Maturity, and Grain Yield in Tropical Maize (*Zea mays* L.) under Multiple Abiotic Stresses," Crop Science, Jan.-Feb. 2017, vol. 57, pp. 229-242.
UniProt, Database Accession No. COP2L8, dated May 5, 2009, 2 pages.
UniProtKB Entry A0A1D6IJ30_MAIZE, [online], Nov. 30, 2016, 1 page, [Retrieved on Sep. 20, 2019] Retrieved from the URL: https://www.uniprot.org/uniprot/A0A1D6IJ30.txt.
Wang L., et al., "Comparative Analyses of C4 and C3 Photosynthesis in Developing Leaves of Maize and Rice," Nature Biotechnology, Nov. 2014, vol. 32, No. 11, pp. 1158-1170.
Ware D., "Agamous-like MADS-Box Protein AGL8 [*Zea mays*]," Genbank locus: ONM59473, Feb. 7, 2017, 1 page.
Wei B., et al., "Functional Divergence of Two Duplicated D-lineage MADS-box Genes BdMADS2 and BdMADS4 from Brachypodium Distachyon," Journal of Plant Physiology, 2013, vol. 170, pp. 424-431.
Wei B., et al., "Novel microRNAs Uncovered by Deep Sequencing of Small RNA Transcriptomes in Bread Wheat (*Triticum aestivum* L.) and *Brachypodium distachyon* (L.) Beauv," Functional & Integrative Genomics, 2009, vol. 9, pp. 499-511.
Whisstock J.C., et al., "Prediction of Protein Function from Protein Sequence and Structure," Quarterly Reviews of Biophysics, Aug. 2003, vol. 36, No. 3, pp. 307-340.
Wu J., et al., "Overexpression of zmm28 Increases Maize Grain Yield in the Field," Proceedings of the National Academy of Sciences, Nov. 19, 2019, vol. 116, No. 47, pp. 23850-23858, DOI: 10.1073/pnas.1902593116, ISSN 0027-8424, XP055654707.
Xing S., et al., "Techniques for the Analysis of Protein-Protein Interactions in Vivo," Plant Physiology, Jun. 2016, vol. 171, pp. 727-758.
Yadav M.R., et al., "Strategies for Improving Nitrogen use Efficiency: A Review," Agricultural Reviews, 2017, vol. 38, No. 1, pp. 29-40.
Yoo S-D., et al., "*Arabidopsis* Mesophyll Protoplasts: a Versatile Cell System for Transient Gene Expression Analysis," Nature Protocols, 2007, vol. 2, No. 7, pp. 1565-1573, 9 Pages.
Yu Y. T., et al., "Identification of a Major Quantitative Trait Locus for Ear Size Induced by Space Flight in Sweet Corn," Genetics and Molecular Research, 2014, vol. 13, No. 2, pp. 3069-3078.
Zastrow-Hayes G.M., et al., "Southern-by-Sequencing: A Robust Screening Approach for Molecular Characterization of Genetically Modified Crops," The Plant Genome, Mar. 13, 2015, vol. 8, No. 1, pp. 1-15.
Zhang J.Z., "Overexpression Analysis of Plant Transcription Factors," Current Opinion in Plant Biology, 2003, vol. 6, pp. 430-440.
Zhang Y., et al., "Model-Based Analysis of ChIP-Seq (MACS)," Genome Biology, Sep. 17, 2008, vol. 9, Issue No. 9(R137), pp. R137.1-R137.9, 09 Pages.
Zhao Q., et al., "MADS-Box Genes of Maize: Frequent Targets of Selection During Domestication," Genetics Research (Cambridge), Feb. 2011, vol. 93, No. 1, pp. 65-75, 19 pages.
Zhao Y., et al., "Whole-Genome Survey and Characterization of MADS-Box Gene Family in Maize and Sorghum," Plant Cell Tissue Organ Culture, 2011, vol. 105, pp. 159-173.
Zheng Z.L., et al., "Carbon and Nitrogen Nutrient Balance Signaling in Plants," Plant Signaling & Behavior, Jul. 2009, vol. 4, No. 7, pp. 584-591.

* cited by examiner

SEQUENCE LISTING

<160> NUMBER OF SEQ ID NOS: 38

<210> SEQ ID NO 1
<211> LENGTH: 251

```
<212> TYPE: PRT
<213> ORGANISM: Zea mays

<400> SEQUENCE: 1

Met Gly Arg Gly Pro Val Gln Leu Arg Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Leu Ile Val Phe
        35                  40                  45

Ser Thr Lys Gly Lys Leu Tyr Glu Tyr Ser Ser His Ser Ser Met Glu
    50                  55                  60

Gly Ile Leu Glu Arg Tyr Gln Arg Tyr Ser Phe Glu Glu Arg Ala Val
65                  70                  75                  80

Leu Asn Pro Ser Ile Glu Asp Gln Ala Asn Trp Gly Asp Glu Tyr Val
                85                  90                  95

Arg Leu Lys Ser Lys Leu Asp Ala Leu Gln Lys Ser Gln Arg Gln Leu
            100                 105                 110

Leu Gly Glu Gln Leu Ser Ser Leu Thr Ile Lys Glu Leu Gln Gln Leu
        115                 120                 125

Glu Gln Gln Leu Asp Ser Ser Leu Lys His Ile Arg Ser Arg Lys Asn
    130                 135                 140

Gln Leu Met Phe Asp Ser Ile Ser Ala Leu Gln Lys Lys Glu Lys Ala
145                 150                 155                 160

Leu Thr Asp Gln Asn Gly Val Leu Gln Lys Phe Met Glu Ala Glu Lys
                165                 170                 175

Glu Lys Asn Lys Ala Leu Met Asn Ala Gln Leu Arg Glu Gln Gln Asn
            180                 185                 190

Gly Ala Ser Thr Ser Ser Pro Ser Leu Ser Pro Ile Val Pro Asp
        195                 200                 205

Ser Met Pro Thr Leu Asn Ile Gly Pro Cys Gln His Arg Gly Ala Ala
210                 215                 220

Glu Ser Glu Ser Glu Pro Ser Pro Ala Pro Ala Gln Ala Asn Arg Gly
225                 230                 235                 240

Asn Leu Pro Pro Trp Met Leu Arg Thr Val Lys
                245                 250

<210> SEQ ID NO 2
<211> LENGTH: 251
<212> TYPE: PRT
<213> ORGANISM: Zea mays

<400> SEQUENCE: 2

Met Gly Arg Gly Pro Val Gln Leu Arg Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Leu Ile Val Phe
        35                  40                  45

Ser Thr Lys Gly Lys Leu Tyr Glu Tyr Ser Ser His Ser Ser Met Glu
    50                  55                  60

Gly Ile Leu Glu Arg Tyr Gln Arg Tyr Ser Phe Glu Glu Arg Ala Val
65                  70                  75                  80

Leu Asn Pro Ser Ile Glu Asp Gln Ala Asn Trp Gly Asp Glu Tyr Val
                85                  90                  95
```

```
Arg Leu Lys Ser Lys Leu Asp Ala Leu Gln Lys Ser Gln Arg Gln Leu
            100                 105                 110

Leu Gly Glu Gln Leu Ser Ser Leu Thr Ile Lys Glu Leu Gln Gln Leu
        115                 120                 125

Glu Gln Gln Leu Asp Ser Ser Leu Lys His Ile Arg Ser Arg Lys Asn
    130                 135                 140

Gln Leu Met Phe Asp Ser Ile Ser Ala Leu Gln Lys Lys Glu Lys Ala
145                 150                 155                 160

Leu Thr Asp Gln Asn Gly Val Leu Gln Lys Phe Met Glu Ala Glu Lys
                165                 170                 175

Glu Lys Asn Lys Ala Leu Met Asn Ala Gln Leu Arg Glu Gln Gln Asn
            180                 185                 190

Gly Ala Ser Thr Ser Ser Pro Ser Leu Ser Pro Pro Ile Val Pro Asp
        195                 200                 205

Ser Met Pro Thr Leu Asn Ile Gly Pro Cys Gln Pro Arg Gly Gly Ala
    210                 215                 220

Glu Ser Glu Ser Glu Pro Ser Pro Ala Pro Ala Gln Ala Asn Arg Gly
225                 230                 235                 240

Asn Leu Pro Pro Trp Met Leu Arg Thr Val Lys
                245                 250

<210> SEQ ID NO 3
<211> LENGTH: 251
<212> TYPE: PRT
<213> ORGANISM: Zea mays

<400> SEQUENCE: 3

Met Gly Arg Gly Pro Val Gln Leu Arg Arg Ile Glu Asn Lys Ile Asn
1               5                   10                  15

Arg Gln Val Thr Phe Ser Lys Arg Arg Asn Gly Leu Leu Lys Lys Ala
            20                  25                  30

His Glu Ile Ser Val Leu Cys Asp Ala Glu Val Ala Leu Ile Val Phe
        35                  40                  45

Ser Thr Lys Gly Lys Leu Tyr Glu Tyr Ser Ser His Ser Ser Met Glu
50                  55                  60

Gly Ile Leu Glu Arg Tyr Gln Arg Tyr Ser Phe Glu Glu Arg Ala Val
65                  70                  75                  80

Leu Glu Pro Ser Ile Glu Asp Gln Ala Asn Trp Gly Asp Glu Tyr Val
                85                  90                  95

Arg Leu Lys Ser Lys Leu Asp Ala Leu Gln Lys Ser Gln Arg Gln Leu
            100                 105                 110

Leu Gly Glu Gln Leu Ser Ser Leu Thr Ile Lys Glu Leu Gln Gln Leu
        115                 120                 125

Glu Gln Gln Leu Asp Ser Ser Leu Lys His Ile Arg Ser Arg Lys Asn
    130                 135                 140

Gln Leu Met Phe Asp Ser Ile Ser Ala Leu Gln Lys Lys Glu Lys Ala
145                 150                 155                 160

Leu Thr Asp Gln Asn Gly Val Leu Gln Lys Phe Met Glu Ala Glu Lys
                165                 170                 175

Glu Lys Asn Lys Ala Leu Met Asn Ala Gln Leu Arg Glu Gln Gln Asn
            180                 185                 190

Gly Ala Ser Thr Ser Ser Pro Ser Leu Ser Pro Pro Ile Val Pro Asp
        195                 200                 205

Ser Met Pro Thr Leu Asn Ile Gly Pro Cys Gln His Arg Gly Ala Ser
    210                 215                 220
```

Glu Ser Glu Ser Glu Pro Ser Pro Ala Pro Ala Gln Ala Asn Arg Gly
225                 230                 235                 240

Asn Leu Pro Pro Trp Met Leu Arg Thr Val Lys
                245                 250

<210> SEQ ID NO 4
<211> LENGTH: 248
<212> TYPE: PRT
<213> ORGANISM: Zea mays

<400> SEQUENCE: 4

Met Gly Arg Gly Lys Val Glu Leu Lys Arg Ile Glu Asn Lys Ile Ser
1               5                   10                  15

Arg Gln Val Thr Phe Ala Lys Arg Arg Asn Gly Leu Leu Lys Lys Ala
                20                  25                  30

Tyr Glu Leu Ser Leu Leu Cys Asp Ala Glu Val Ala Leu Ile Ile Phe
            35                  40                  45

Ser Gly Arg Gly Arg Leu Phe Glu Phe Ser Ser Ser Trp Tyr Asp
    50                  55                  60

Ala Arg Ala Leu Arg Met Tyr Lys Thr Leu Glu Arg Tyr Arg Ser Ser
65                  70                  75                  80

Asn Tyr Ser Gln Glu Val Lys Thr Pro Leu Asp Thr Glu Ile Lys Tyr
                85                  90                  95

Gln Asp Tyr Leu Lys Leu Arg Thr Arg Val Glu Phe Leu Gln Thr Thr
            100                 105                 110

Gln Arg Asn Ile Leu Gly Glu Asp Leu Gly Pro Leu Ser Met Lys Glu
        115                 120                 125

Leu Glu Gln Leu Glu Asp Gln Ile Glu Ile Ser Leu Lys His Ile Ser
    130                 135                 140

Ser Arg Lys Asn Gln Met Leu Leu Asp Gln Leu Phe Asp Leu Lys Ser
145                 150                 155                 160

Lys Glu Gln Glu Leu Leu Asp Leu Asn Lys Asp Leu Arg Lys Gln Leu
                165                 170                 175

Gln Glu Thr Arg Pro Glu Asn Ala Leu Arg Val Ser Trp Glu Glu Gly
            180                 185                 190

Gly His Ser Gly Ala Ser Gly Asn Val Leu Asp Pro Tyr Gln Gly Leu
        195                 200                 205

Leu Gln His Leu Asp Asn Asp Pro Ser Leu Gln Phe Gly Tyr His His
    210                 215                 220

Gln Ala Tyr Met Asp Gln Leu Asn Asn Glu Asp Leu Val Asp Pro Asn
225                 230                 235                 240

Glu His Gly Arg Ser Gly Trp Ile
                245

<210> SEQ ID NO 5
<211> LENGTH: 1653
<212> TYPE: DNA
<213> ORGANISM: Zea mays

<400> SEQUENCE: 5
gtgagtggtg gggtcgatga ccctgatgtt tgtggtctct ggttccaaga atctttgtct      60
ctctttatga taataacttc ttttgtcgtc ttttctgtt tactttgact caggggcagt     120
gctttgattc tcacggtcgg tccttttgac tgagtgactg acatgtttc ttctgtagca     180 ttgtacaaca tgtactttgt gcaagctaca aggtcacatt ttttgaagca tagattcttt     240

```
cccccaaaca atttatacaa atatgcaagg ctacacttct tgtatttcta taacattgta    300
cattcatgac agaggctcaa aagcttgtaa attttgtgca ggtttaattc atgtaaagtt    360
cccttgtaga gtcatgacaa catcgtacta taaaattatt ctacaaaaac cacacatgac    420
ccccatgtta tttggtgaca atacagaaac cacacatcta gtgatgatat aacactgtac    480
agaagccaca aattataata tataaaacac tatacaaagt atccaaataa agcctaatag    540
gtatggaggg taacctgaat cttttcctaat aataatgaat aatctacaat aatgatttgt    600
ttggacaaag agaattaaac ggtattgagt gggctaaaat tccttgttat tcaaacccct    660
caatcacagt ttctccgagg gaaaagaaa caggggagga cactcaggct gttcacaata    720
gggatttcat atcgctcttt ccaacaatgc cacatcatca aaagtgttat gaaactaaaa    780
atgaaataat acttctcaat gcaaactttc attttcatag attaatatac taattaaatg    840
atgcaactaa ataaccaata gatgttagta aaatatggta agattaaaca aaccactatc    900
aatggacatt tcacatagtt tccaagactt tgaaaacggg ttgacatgat ttcatccaca    960
tcaaactaat tttatctctg aaacccattc attttaaatg atatggcata acgtccaaaa    1020
tgctgacgtg acataccatt aaatgtgcat gaaactccca taaaactttt attgataata    1080
gcctcacaga catccggtcc tacaccgtg tggacccatc agccagacgc cctgcagcaa    1140
acgcgacgtt tgacttgcca tctcgctccc ttgtgcccga ccgaccctgg aaggctggac    1200
tggaactgga acaagcaaaa tggaaaaaac catatctcac cactgaaccg cacccttccg    1260
gcccacgcca ggctcgacca atccctgccc cgcgcgccct gacgagcgca tcactcgaac    1320
gccggcctcg ctaggcccat ccttctggcc cgcaataacg atccccgtca tgatccgacg    1380
gtctagctgc ctccacgccg ctccaaaacc cccgcgtcca atcaaaacac gacagcggga    1440
cgagcgaaac caccgtggtt tcgccaaacc gctttccttc ccatctaaaa ccgcccctc    1500 ccttcctctt ctcctagctc tcttgcctgc gcaccactcg agtcgagact cgagaggcac    1560
ctgatctttc cttcccgtct tcctcccaca cgtccccatc accattgctg cgacgagagt    1620
gagcgggaga gggtaggtgg cgaggcggcg gag                                 1653
```

<210> SEQ ID NO 6
<211> LENGTH: 1653
<212> TYPE: DNA
<213> ORGANISM: Zea mays

<400> SEQUENCE: 6

```
gtgagtggtg gggtcgatga ccctgatgtt tgtggtctct ggttccaaga atctttgtct     60
ctctttatga taataacttc ttttgtcgtc cttttctgtt tactttgact caggggcagt    120
gctttgattc tcacggtcgg tccttttgac tgagtgactg acatgtttc ttctgtagca    180 ttgtacaaca tgtactttgt gcaagctaca aggccacatt ttttgaagca tagattctttt    240 cccccaaaca atttatacaa atatgcaagg ctacacttct tgtatttcta taacattgta    300
cattcatgac agaggctcaa aagcttgtaa attttgtgca ggtttaattc atgtaaagtt    360
cccttgtaga gtcatgacaa catcgtacta taaaattatt ctacaaaaac cacacatgac    420
ccccatgtta tttggtgaca atacagaaac cacacatcta gtgatgatat aacactgtac    480
agaagccaca aattataata tataaaacac tatacaaagt atccaaataa agcctaatag    540
gtatggaggg taacctgaat cttttcctaat aataatgaat aatctacaat aatgatttgt    600
ttggacaaag agaattaaac ggtattgagt gggctaaaat tccttgttat tcaaacccct    660
caatcacagt ttctccgagg gaaaagaaa caggggagga cactcaggct gttcacaata    720
```

-continued

```
gggatttcat atcgctcttt ccaacaatgc cacatcatca aaagtgttat gaaactaaaa      780
atgaaataat acttctcaat gcaaactttc attttcatag attaatatac taattaaatg      840
atgcaactaa ataaccaata gatgttagta aaatatggta agattaaaca aaccactatc      900
aatggacatt tcacatagtt tccaagactt tgaaaacggg ttgacatgat ttcatccaca      960
tcaaactaat tttatctctg aaacccattc attttaaatg atatggcata acgtccaaaa     1020
tgctgacgtg ataccatt aaatgtgcat gaaactccca taaaacttttt attgataata     1080 gcctcacaga catccggtcc tacacccgtg tggacccatc agccagacgc cctgcagcaa     1140
acgcgacgtt tgacttgcca tctcgctccc ttgtgcccga ccgacccctgg aaggctggac     1200 tggaactgga acaagcaaaa tggaaaaaac catatctcac cactgaaccg caccccttccg     1260 gcccacgcca ggctcgacca atccctgccc cgcgcgccct gacgagcgca tcactcgaac     1320
gccggcctcg ctaggcccat ccttctggcc cgcaataacg atccccgtca tgatccgacg     1380
gtctagctgc ctccacgccg ctccaaaacc cccgcgtcca atcaaaacac dacagcggga     1440
cgagcgaaac caccgtggtt tcgccaaacc gctttccttc ccatctaaaa ccgcccctc     1500 ccttcctctt ctcctagctc tcttgcctgc gcaccactcg agtcgagact cgagaggcac     1560
ctgatctttc cttcccgtct tcctcccaca cgtccccatc accattgctg cgacgagagt     1620
gagcgggaga gggtaggtgg cgaggcggcg gag                                   1653
```

<210> SEQ ID NO 7
<211> LENGTH: 1791
<212> TYPE: DNA
<213> ORGANISM: Zea mays

<400> SEQUENCE: 7

```
aaagaggtgc ctagtttacc ggaaagatga caatgaggtc atcgcaaaaa gggggagtgg       60
gtggcggtga agtatttaaa agggaccatg gtccggtggt agtgcgcaag gaggcgggcc      120
cgcgtgcgag gggcacgggt gggtggtggg gttgacgacc ctaaagtttg tggtctatag      180
ttccaagaat ctttgcctct ctgtattgta ataactcatt tgtcctctt tttctgttta      240 cttagactca ggggcagtgc tctgattctc acggtcggtc cttttggctg agcggcaaga      300
catgtttctt ctgtagcatt gtacaacatg tactttgtgc aagctacaag gccacatttt      360
ttgaagcata gattctttcc cccaaacaat ttatacaaat atgcaaggct acacttcttg      420
tatttctata acattgtaca ttcatgacag aggctcaaaa gcttgtaaat tttgtgcagg      480
tttaattcat gtaaagttcc cttgtagagt catgacaaca tcgtactata aaattattct      540
acaaaaacca cacatgaccc ccatgttatt tggtgacaat acagaaacca cacatctagt      600
gatgatataa cactgtacag aagccacaaa ttataatata taaaacacta tacaaagtat      660
ccaaataaag cctaataggt atggagggta acctgaatct ttcctaataa taatgaataa      720
tctacaataa tgatttgttt ggacaaagag aattaaacgg tattgagtgg gctaaaattc      780
cttgttattc aaaaccctca atcacagttt ctccgaggga aaagaaaca ggggaggaca      840 ctcaggctgt tcacaatagg gatttcatat cgctctttcc aacaatgcca catcatcaaa      900
agtgttatga aactaaaaat gaaataatac ttctcaatgc aaactttcat tttcatagat      960
taatatacta attaaatgat gcaactaaat aaccaataga tgttagtaaa atatggtaag     1020
attaaacaaa ccactatcaa tggacatttc acatagtttc caagactttg aaaacgggtt     1080
gacatgattt catccacatc aaactaattt tatctctgaa acccattcat tttaaatgat     1140
```

| | |
|---|---|
| atggcataac gtccaaaatg ctgacgtgac ataccattaa atgtgcatga aactcccata | 1200 |
| aaacttttat tgataatagc ctcacagaca tccggtccta cacccgtgtg gacccatcag | 1260 |
| ccagacgccc tgcagcaaac gcgacgtttg acttgccatc tcgctcccct gtgcccgacc | 1320 |
| gaccctggaa ggctggactg gaactggaac aagcaaaatg gaaaaaacca tatctcacca | 1380 |
| ctgaaccgca cccttccggc ccacgccagg ctcgaccaat ccctgccccg cgcgccctga | 1440 |
| cgagcgcatc actcgaacgc cggcctcgct aggcccatcc ttctggcccg caataacgat | 1500 |
| ccccgtcatg atccgacggt ctagctgcct ccacgccgct ccaaaacccc cgcgtccaat | 1560 |
| caaaacacga cagcgggacg agcgaaacca ccgtggtttc gccaaaccgc tttccttccc | 1620 |
| atctaaaacc gcccccctccc ttcctcttct cctagctctc ttgcctgcgc accactcgag | 1680 |
| tcgagactcg agaggcacct gatctttcct tcccgtcttc ctcccacacg tccccatcac | 1740 |
| cattgctgcg acgagagtga gcgggagagg gtaggtggcg aggcggcgga g | 1791 |

<210> SEQ ID NO 8
<211> LENGTH: 2465
<212> TYPE: DNA
<213> ORGANISM: Zea mays

<400> SEQUENCE: 8

| | |
|---|---|
| gtatacgtat tcgatcccct tgttcctgcc ggccggttgc tacgatcgcc cgctcggggt | 60 |
| ttgaagcgct gggtgtgctt cgacgcatga tttttggatc atttttcatg tgtcaatccg | 120 |
| ctgccggccg gtttctatgt tcgcccgctt ggtgtttgta gtgctgggtg tcgacgcatg | 180 |
| attttggaat cacttttcat gtgtcaatct gctgcgttca tcgaacttgt atggggattg | 240 |
| agctgtggga ggtgtttgta gaacgtagac acatgcatgt atggttgtta ttacgtgtta | 300 |
| gttctatgtg gattaattat agttatttcc atggacactg ctcggccggt caacgatcgc | 360 |
| ttcagatgat tcaaccgtgg aatcatcgct tgctggttaa ttcgttcgta cgtacacagt | 420 |
| ggcatacgca aattgagcgg gatactgtag ttttgcaaac tgagaatgtt atgagtagtg | 480 |
| gtgctggtga atgtcaatta gcccatgcaa attatgtccc aagctttgag gtgtgactga | 540 |
| ctaatggcta gtatatagaa agtggtcagg attattattt ggttcataaa tactgtgaag | 600 |
| aggtgaggat cagtcgctgg aaggattctg attgccaaaa tatattttttt tcatcatgcg | 660 |
| atcaaactct tcagtatcaa gtaggtgtat tatttcagca taatttattg caaaggaaac | 720 |
| acttcttttg tcttttgcat gcatgatgaa ggatatgctt atcagtatct ctatggtggt | 780 |
| gtttggttca ttgcatggag tggttaacgt aacctgaacg gatcccacga ctattggtta | 840 |
| cagtgcaaca gagatacgtt tggttagtta acgtcgaaaa gatatggctc cgtatccatt | 900 |
| tgtgaatcgt tacggactga cccaaccaaa cagaaaagaa agggaataga tggatcacag | 960 |
| ataaaaatgt cataccaaac agcctctata ctatttctg cttcgatgtt ccttgtatat | 1020 |
| gtgcatcttg tcgattttc agatagcctg tgataaatgt gcacaaattt ctatacaaac | 1080 |
| agctgttgtg gtcatgctgt agaagattca tatggagaag tgttattaat tatctgaata | 1140 |
| ttttcagaaa ttccagaaga acaattctgc tcttgtgtgg tgtctctgat tcatgcatgt | 1200 |
| gtcatatatt aagagattgt ccctgttcca catttttagta ttatataaac ggtatacaag | 1260 |
| gtgatcataa tatttaaaca ttagtttgat tttttggcac atatttcatt acagtttcaa | 1320 |
| atttggttcc ttaaacaaca cggctatctt agaaaataga tgcttgatta tagcaaaaat | 1380 |
| tgaccttatg ctgctataag ttagattcta ggaggttaaa ttggcatgag tacatattct | 1440 |
| gaccatgcaa catattcata tataaccgat cgattcaggg aaaatgtcac tgagttaact | 1500 |

```
taccctcccc atactggatt atctgtactc tctagtgctg agacaaaat atgtatgtta    1560 aaaaataata agcacgtttt agcttttgca cacgagtgat atgtgttggt gataagatcc    1620
gaagttgata gagattgtgg cttgagtcac cgcaaaattt gatgacattt tctttagctg    1680
aaactacaag tacccatgcc ggtaatgaat tttattttaa aaataatat gatatggctt    1740 aatgtagatc cattttata tgttgtggat tatagaaaac catgctaatt acaactacga    1800
atttgaattt gaaatatcaa tagattccta caaaaatgta tatcactata cttttgctaa    1860
ttttctaaag atgttacaaa atttactgtt caaacccgac aaagaaggta gatgccaaat    1920
ctgtctaaaa gattatatta gatcgatcca cagattatag tatcaaagtg atggaaaaca    1980
ttgtttgcac aaacaactga gtagctcgct acattttaga gctatttta catcattatt    2040 tactcttgac ttgttttatt gttctaaaat acccttctg agttcatgta tgaactatat    2100
atgaagcacc atctgttcat taagtaatga cccacttatg tgtgcatgtg atgacagacg    2160
ttgttccata accatgcttg catctagcta tgcatgtgat ttaaggttag ctgtccaatg    2220
tcttttgcaa ttctggaatc gggagaatat acttctatat atatatctta catttatcaa    2280
atagggagaa attaaatctt gatatcttga acgttgttca tcgtgaattt tgtcgttttg    2340
tatgcaatac taatatactt catctagtaa tacaaaaggt acaagaaaaa gaaaattgca    2400
cctggctatt tgtcttaata tattatgctg gaacatgaca ttgctatatg atacttcttt    2460
tgcag                                                                2465

<210> SEQ ID NO 9
<211> LENGTH: 2456
<212> TYPE: DNA
<213> ORGANISM: Zea mays

<400> SEQUENCE: 9
gtatacgtat tcgatcccct tgttcctgcc ggccggttgc tacgatcgcc cgctcggggt      60
ttgaagcgct gggtgtgctt cgacgcatga ttttttggatc attttcatg tgtcaatccg     120 ctgccggccg gtttctatgt tcgcccgctt ggtgtttgta gtgctgggtg tcgacgcatg     180 atttttggaat cacttttcat gtgtcaatct gctgcgttca tcgaacttgt atggggattg     240
agctgtggga ggtgtttgta gaacgtagac acatgcatgt atggttgtta ttacgtgtta     300
gttctatgtg gattaattat agttatttcc atggacactg ctcggccggt caacgatcgc     360
ttcagatgat tcaaccgtgg aatcatcgct tgctggttaa ttcgttcgta cgtacacagt     420
ggcatacgca aattgagcgg gatactgtag ttttgcaaac tgagaatgtt atgagtagtg     480
gtgctggtga atgtcaatta gcccatgcaa attatgtccc aagctttgag gtgtgactga     540
ctaatggcta gtatatagaa agtggtcagg attattattt ggttcataaa tactgtgaag     600
aggtgaggat cagtcgctgg aaggattctg attgccaaaa tatattttt tcatcatgcg     660 atcaaactct tcagtatcaa gtaggtgtat tatttcagca taatttattg caaaggaaac    720
acttcttttg tcttttgcat gcatgatgaa ggatatgctt atcagtatct ctatggtggt    780
gtttggttca ttgcatggag tggttaacgt aacctgaacg gatcccacga ctattggtta    840
cagtgcaaca gagatacgtt tggttagtta acgtcgaaaa gatatggctc cgtatccatt    900
tgtgaatcgt tacggactga cccaaccaaa cagaaaagaa agggaataga tggatcacag    960
ataaaaatgt cataccaaac agcctctata ctatttctg cttcgatgtt ccttgtatat   1020
gtgcatcttg tcgattttc agatagcctg tgataaatgt gcacaaattt ctatacaaac   1080
```

-continued

```
agctgttgtg gtcatgctgt agaagattca tatggagaag tgttattaat tatctgaata      1140
ttttcagaaa ttccagaaga acaattctgc tcttgtgtgg tgtctctgat tcatgcatgt      1200
gtcatatatt aagagattgt ccctgttcca cattttagta ttatataaac ggtatacaag      1260
gtgatcataa tatttaaaca ttagtttgat tttttggcac atatttcatt acagtttcaa      1320
atatggttcc ttaaacaaca cggctatctt agaaaataga tgcttgatta tagcaaaaat      1380
tgaccttatg ctgctataag ttagattcta ggaggttaaa ttggcatgag tacatattct      1440
gaccatgcaa catattcata tataaccgat cgattcaggg aaaatgtcac tgagttaact      1500 tacccctcccc acactggatt atctgtaact ctctagtgct ggagacaaaa tatgtatgtt      1560
aaaaaataat aagcacgttt tagcttttgc acacgagtga tatgtgttgg tgatatgatc      1620
cgaagttgat agagattgtg gcttgagtca ccgcaaaatt tgatgacatt ttctttagct      1680
gaacccatgc cggtaatgaa ttttatttta aaaaataata tgatatggct taatgtagat      1740 ccattttat atgttgtgga ttatagaaaa ccatgctaat tacaactacg agtttgaatt      1800
tgaaatatca atagattcct acaaaaatgt atatcactat acttttgcta atttactaaa      1860
gatgttacaa actttactgt tcaaacccga caaaaaaggt agatgccaaa tctgtctaaa      1920
agattatatt agatcgatcc acagattata gtatcaaagt gatggaaaac attgtttgca      1980
caaacaactg agtagctcgc tacattttag agctattttt acatcattat ttactcttga      2040
cttgttttat tgttctaaaa tacccttttct gagttcatgt atgaactata tatgaagcac      2100
catctgttca ttaagtaatg acccacttat gtgtgcatgt gatgacagac gttgttccat      2160
aaccatgctt gcatctagct atgcatgtga ttcaaggtta gctgtccaat gtcttttgca      2220
attctggaat cgggagaata tacttgtata tatatatctt acatttatca aatagggaga      2280
aattaaatct tgatatcttg aacgttgttc atcgtgaatt ttgtcgtttt gtatgcaata      2340
ctaatatact tcatctagta atacaaaagg tacaagaaaa agaaaattgc acctggctat      2400
ttgtcttaat atattatgct ggaacatgac attgctatat gatacttctt ttgcag         2456
```

<210> SEQ ID NO 10
<211> LENGTH: 2469
<212> TYPE: DNA
<213> ORGANISM: Zea mays

<400> SEQUENCE: 10

```
gtatacgtat tcgatcccct tgttcctgcc ggccggttgc tacgatcgcc cgctcggggt        60
ttgaagcgct gggtgtgctt cgacgcatga ttttttggatc attttttcatg tgtcaatccg       120 ctgccggccg gtttctatgt tcgcccgctt ggtgtttgta gtgctgggtg tcgacgcatg       180
attttggaat cacttttcat gtgtcaatct gctgcgttca tcgaacttgt atggggattg       240
agctgtggga ggtgtttgta gaacgtagac acatgcatgt atggttgtta ttacgtgtta       300
gttctatgtg gattaattat agttatttcc atggacactg ctcggccggt caacgatcgc       360
ttcagatgat tcaaccgtgg aatcatcgct tgctggttaa ttcgttcgta cgtacacagt       420
ggcatacgca aattgagcgg gatactgtag ttttgcaaac tgagaatgtt atgagtagtg       480
gtgctggtga atgtcaatta gcccatgcaa attatgtccc aagctttgag gtgtgactga       540
ctaatggcta gtatatagaa agtggtcagg attattattt ggttcataaa tactgtgaag       600
aggtgaggat cagtcgctgg aaggattctg attgccaaaa tatatttttt tcatcatgcg       660
atcaaactct tcagtatcaa gtaggtgtat tatttcagca taatttattg caaaggaaac       720
acttcttttg tcttttgcat gcatgatgaa ggatatgctt atcagtatct ctatggtggt       780
```

-continued

```
gtttggttca ttgcatggag tggttaacgt aacctgaacg gatcccacga ctattggtta      840
cagtgcaaca gagatacgtt tggttagtta acgtcgaaaa gatatggctc cgtatccatt      900
tgtgaatcgt tacggactga cccaaccaaa cagaaaagaa agggaataga tggatcacag      960
ataaaaatgt cataccaaac agcctctata ctattttctg cttcgatgtt ccttgtatat     1020
gtgcatcttg tcgattttc agatagcctg tgataaatgt gcacaaattt ctatacaaac     1080
agctgttgtg gtcatgctgt agaagattca tatggagaag tgttattaat tatctgaata     1140
ttttcagaaa ttccagaaga acaattctgc tcttgtgtgg tgtctctgat tcatgcatgt     1200
gtcatatatt aagagattgt ccctgttcca cattttagta ttatataaac ggtatacaag     1260
gtgatcataa tatttaaaca ttagtttgat tttttggcac atatttcatt acagtttcaa     1320
atttggttcc ttaaacaaca cggctatctt agaaaataga tgcttgatta tagcaaaaat     1380
tgaccttatg ctgctataag ttagattcta ggaggttaaa ttggcatgag tacatattct     1440
gaccatgcaa catattcata taaccgatc gattcaggg aaaatgtcac tgagttaact     1500
taccctcccc atactggatt atctgtactc tctagtgctg gagacaaaat atgtatgtta     1560
aaaaataata agcacgtttt agcttttgca cacgagtgat atgtgttggt gataagatcc     1620
gaagttgata gagattgtgg cttgagtcac cgcaaaattt gatgacattt tctttagctg     1680
aaactacagg tacccatgcc ggtaatgaat tttattttaa aaaataatat gatatggctt     1740
aatgtagatc catttttata tgttgtggat tatagaaaac catgctaatt acaactacga     1800
atttgaattt gaaatatcaa tagattccta caaaaatgta tatcactata cttttgctaa     1860
tttactaaag atgttacaaa atttactgtt caaacccgac aaagaaggta gatgccaaat     1920
ctgtctaaaa gattatatta gatcgatcca cagattatag tatcaaagtg atggaaaaca     1980
ttgtttgcac aaacaactga gtagctcgct acatttaga gctattttta catcattatt     2040
tactcttgac ttgttttatt gttctaaaat acccttctg agttcatgta tgaactatat     2100
atgaagcacc atctgttcat taagtaatga cccacttatg tgtgcatgtg atgacagacg     2160
ttgttccata accatgcttg catctagcta tgcatgtgat ttaaggttag ctgtccaatg     2220
tcttttgcaa ttctggaatc gggagaatat acttctatat atatatatat cttacattta     2280 tcaaatagg agaaattaaa tcttgatatc ttgaacgttg ttcatcgtga attttgtcgt     2340
tttgtatgca atactaatat acttcatcta gtaatacaaa aggtacaaga aaagaaaat     2400 tgcacctggc tatttgtctt aatatattat gctggaacat gacattgcta tatgatactt     2460
cttttgcag                                                             2469
```

<210> SEQ ID NO 11
<211> LENGTH: 2468
<212> TYPE: DNA
<213> ORGANISM: Zea mays

<400> SEQUENCE: 11

```
gtatacgtat tcgatcccct tgttcctgcc ggccggttgc tacgatcgcc cgctcggggt       60
ttgaagcgct gggtgtgctt cgacgcatga ttttttggatc attttttcatg tgtcaatccg      120 ctgccggccg gtttctatgt tcgcccgctt ggtgtttgta gtgctgggtg tcgacgcatg      180
attttggaat cacttttcat gtgtcaatct gctgcgttca tcgaacttgt atgggattg      240 agctgtggga ggtgtttgta gaacgtagac acatgcatgt atggttgtta ttacgtgtta      300
gttctatgtg gattaattat agttatttcc atggacactg ctcggccggt caacgatcgc      360
```

| | |
|---|---|
| ttcagatgat tcaaccgtgg aatcatcgct tgctggttaa ttcgttcgta cgtacacagt | 420 |
| ggcatacgca aattgagcgg gatactgtag ttttgcaaac tgagaatgtt atgagtagtg | 480 |
| gtgctggtga atgtcaatta gcccatgcaa attatgtccc aagctttgag gtgtgactga | 540 |
| ctaatggcta gtatatagaa agtggtcagg attattattt ggttcataaa tactgtgaag | 600 |
| aggtgaggat cagtcgctgg aaggattctg attgccaaaa tattttttt attcatcatg | 660 |
| cgatcaaact cttcagtatc aagtaggtgt attatttcag cataatttat tgcaaaggaa | 720 |
| gcacttcttt tgtcttttgc atgcatgatg aaggatatgc ttatcagtat cactatggtg | 780 |
| gtgtttggtt cattgcatgg agtggttaac gtaacctgaa cggatcccac agctattggt | 840 |
| tacagtgcaa cagagatatg tttggttagt taacgtcgaa aagatacggc tccgtatcca | 900 |
| tttgtgaatc gttacggact gacccaacca aacagaaaag aaatggaata gatggatcac | 960 |
| agataaaaat gtcataccaa acaacctcta tactattttc tgcttcgatg ttccttgtat | 1020 |
| atgtgcatct tgtcgatttt tcagatagcc tgtgataaac gtgcacaaat ttctatacaa | 1080 |
| acagctgttg tggtcatgct gtagaagatt catatggaga agtgttatta attatctgaa | 1140 |
| tattttcaga aattccataa gatcaattct gctcttgtgt ggtgtctctg attcatgcat | 1200 |
| gtgtcatata ttaagagatt gtccctgttc cacattttag tattatataa acggtatgca | 1260 |
| aggtgatcat aatacttaaa cattagtttg attttttggc acatatttca ttacagtttc | 1320 |
| aaatttggtt ccttaaacaa cacggctatc ttagaaaata gatgcttgat tatagcaaaa | 1380 |
| attgacctta tgctgctata agttagattc taggaggtta aattggcatg agtacatatt | 1440 |
| ctgaccatgc aacatattca tatataactg atcgattcag ggaaaatgtc actgagttaa | 1500 |
| cttaccctcc ccacactgga ttatctgtac tctctagtgc tggagacaaa atatgtatgt | 1560 |
| taaaaaataa taagcacgtt ttagcttttg cacacgagtg atatgtgttg gtgataagat | 1620 |
| ccgaagttga tagagattgt ggcttgagtc accgcaaaat ttgatgacat tttctttagc | 1680 |
| tgaaactaca ggtcacccat gccggtaatg aattttattt taaaaaataa tatgatatgg | 1740 |
| cttaatgtag atccattttt atatgttgtg gattatagaa aaccatgcta attacaacta | 1800 |
| cgagtttgaa tttgaaatat caatagattc ctacaaaaat gtatatcact atacttatgc | 1860 |
| taatttacta aagatgttac aaactttact gttcaaaccc gacaaagaag gtagatgcta | 1920 |
| aatctgtcta aaatattata ttagatcgat ccacagatta ttgtatcaaa gtgatggaaa | 1980 |
| acattgtttg cacaaacaac tgagtagctc gctacatttt agagctattt ttacatcatt | 2040 |
| atgtactctt gacttgtttt attgttctaa aatacccttt ctgagttcat gtatgaacta | 2100 |
| tatatgaagc accatctgtt cattaagtaa tgacccactt atgtgtgcat gtgatgacag | 2160 |
| acgttgttcc ataaccatgc ttgcatctag ctatgcatgt gattcaaggt tagctgtcca | 2220 |
| atgtcttttg caattctgga atcgggagaa tatacttgta tatatatatc ttacatttat | 2280 |
| caaataggga gaaattaaat cttgatatct tgaacgttgt tcatcgtgaa ttttgtcgct | 2340 |
| ttatatgcaa tactaatata cttcatctag taatacaaaa ggtacaagaa aaagaaaatt | 2400 |
| gcacctggct atttgtctta atatattatg ctggaacatg acattgctat atgatacttc | 2460 |
| ttttgcag | 2468 |

<210> SEQ ID NO 12
<211> LENGTH: 2469
<212> TYPE: DNA
<213> ORGANISM: Zea mays

<400> SEQUENCE: 12

```
gtatacgtat tcgatcccct tgttcctgcc ggccggttgc tacgatcgcc cgctcggggt    60
ttgaagcgct gggtgtgctt cgacgcatga tttttggatc attttcatg tgtcaatccg    120 ctgccggccg gtttctatgt tcgcccgctt ggtgtttgta gtgctgggtg tcgacgcatg    180
attttggaat cacttttcat gtgtcaatct gctgcgttca tcgaacttgt atggggattg    240
agctgtggga ggtgtttgta gaacgtagac acatgcatgt atggttgtta ttacgtgtta    300
gttctatgtg gattaattat agttatttcc atggacactg ctcggccggt caacgatcgc    360
ttcagatgat tcaaccgtgg aatcatcgct tgctggttaa ttcgttcgta cgtacacagt    420
ggcatacgca aattgagcgg gatactgtag ttttgcaaac tgagaatgtt atgagtagtg    480
gtgctggtga atgtcaatta gcccatgcaa attatgtccc aagctttgag gtgtgactga    540
ctaatggcta gtatatagaa agtggtcagg attattattt ggttcataaa tactgtgaag    600
aggtgaggat cagtcgctgg aaggattctg attgccaaaa tatattttt tcatcatgcg     660 atcaaactct tcagtatcaa gtaggtgtat tatttcagca taatttattg caaaggaaac    720
acttcttttg tcttttgcat gcatgatgaa ggatatgctt atcagtatct ctatggtggt    780
gtttggttca ttgcatggag tggttaacgt aacctgaacg gatcccacga ctattggtta    840
cagtgcaaca gagatacgtt tggttagtta acgtcgaaaa gatatggctc cgtatccatt    900
tgtgaatcgt tacggactga cccaaccaaa cagaaaagaa agggaataga tggatcacag    960
ataaaaatgt cataccaaac agcctctata ctattttctg cttcgatgtt ccttgtatat    1020
gtgcatcttg tcgattttc agatagcctg tgataaatgt gcacaaattt ctatacaaac    1080
agctgttgtg gtcatgctgt agaagattca tatggagaag tgttattaat tatctgaata    1140
ttttcagaaa ttccagaaga acaattctgc tcttgtgtgg tgtctctgat tcatgcatgt    1200
gtcatatatt aagagattgt ccctgttcca catttagta ttatataaac ggtatacaag     1260
gtgatcataa tatttaaaca ttagtttgat tttttggcac atatttcatt acagtttcaa    1320
atttggttcc ttaaacaaca cggctatctt agaaaataga tgcttgatta tagcaaaaat    1380
tgaccttatg ctgctataag ttagattcta ggaggttaaa ttggcatgag tacatattct    1440
gaccatgcaa catattcata tataaccgat cgattcaggg aaaatgtcac tgagttaact    1500
taccctcccc atactggatt atctgtactc tctagtgctg gagacaaaat atgtatgtta    1560
aaaaataata agcacgtttt agcttttgca cacgagtgat atgtgttggt gataagatcc    1620
gaagttgata gagattgtgg cttgagtcac cgcaaaattt gatgacattt tctttagctg    1680
aaactacagg tacccatgcc ggtaatgaat tttatttaa aaaataatat gatatggctt     1740
aatgtagatc catttttata tgttgtggat tatagaaaac catgctaatt acaactacga    1800
atttgaattt gaaatatcaa tagattccta caaaaatgta tatcactata cttttgctaa    1860
tttactaaag atgttacaaa atttactgtt caaacccgac aaagaaggta gatgccaaat    1920
ctgtctaaaa gattatatta gatcgatcca cagattatag tatcaaagtg atggaaaaca    1980
ttgtttgcac aaacaactga gtagctcgct acattttaga gctattttta catcattatt    2040
tactcttgac ttgttttatt gttctaaaat acccttctg agttcatgta tgaactatat     2100
atgaagcacc atctgttcat taagtaatga cccacttatg tgtgcatgtg atgacagacg    2160
ttgttccata accatgcttg catctagcta tgcatgtgat ttaaggttag ctgtccaatg    2220
tcttttgcaa ttctggaatc gggagaatat acttctatat atatatatat cttacattta    2280
tcaaataggg agaaattaaa tcttgatatc ttgaacgttg ttcatcgtga attttgtcgt    2340
```

-continued

| | |
|---|---|
| tttgtatgca atactaatat acttcatcta gtaatacaaa aggtacaaga aaaagaaaat | 2400 |
| tgcacctggc tatttgtctt aatatattat gctggaacat gacattgcta tatgatactt | 2460 |
| cttttgcag | 2469 |

<210> SEQ ID NO 13
<211> LENGTH: 2465
<212> TYPE: DNA
<213> ORGANISM: Zea mays

<400> SEQUENCE: 13

| | |
|---|---|
| gtatacgtat tcgatcccct tgttcctgcc ggccggttgc tacgatcgcc cgctcggggt | 60 |
| ttgaagcgct gggtgtgctt cgacgcatga tttttggatc atttttcatg tgtcaatccg | 120 |
| ctgccggccg gtttctatgt tcgcccgctt ggtgtttgta gtgctgggtg tcgacgcatg | 180 |
| attttggaat cactttttcat gtgtcaatct gctgcgttca tcgaacttgt atggggattg | 240 |
| agctgtggga ggtgtttgta gaacgtagac acatgcatgt atggttgtta ttacgtgtta | 300 |
| gttctatgtg gattaattat agttatttcc atggacactg ctcggccggt caacgatcgc | 360 |
| ttcagatgat tcaaccgtgg aatcatcgct tgctggttaa ttcgttcgta cgtacacagt | 420 |
| ggcatacgca aattgagcgg gatactgtag ttttgcaaac tgagaatgtt atgagtagtg | 480 |
| gtgctggtga atgtcaatta gcccatgcaa attatgtccc aagctttgag gtgtgactga | 540 |
| ctaatggcta gtatatagaa agtggtcagg attattattt ggttcataaa tactgtgaag | 600 |
| aggtgaggat cagtcgctgg aaggattctg attgccaaaa tatattttt tcatcatgcg | 660 |
| atcaaactct tcagtatcaa gtaggtgtat tatttcagca taatttattg caaaggaaac | 720 |
| acttcttttg tcttttgcat gcatgatgaa ggatatgctt atcagtatct ctatggtggt | 780 |
| gtttggttca ttgcatggag tggttaacgt aacctgaacg gatcccacga ctattggtta | 840 |
| cagtgcaaca gagatacgtt tggttagtta acgtcgaaaa gatatggctc cgtatccatt | 900 |
| tgtgaatcgt tacggactga cccaaccaaa cagaaaagaa agggaataga tggatcacag | 960 |
| ataaaaatgt cataccaaac agcctctata ctattttctg cttcgatgtt ccttgtatat | 1020 |
| gtgcatcttg tcgatttttc agatagcctg tgataaatgt gcacaaattt ctatacaaac | 1080 |
| agctgttgtg gtcatgctgt agaagattca tatggagaag tgttattaat tatctgaata | 1140 |
| ttttcagaaa ttccagaaga acaattctgc tcttgtgtgg tgtctctgat tcatgcatgt | 1200 |
| gtcatatatt aagagattgt ccctgttcca catttttagta ttatataaac ggtatacaag | 1260 |
| gtgatcataa tatttaaaca ttagtttgat tttttggcac atatttcatt acagtttcaa | 1320 |
| atttggttcc ttaaacaaca cggctatctt agaaaataga tgcttgatta tagcaaaaat | 1380 |
| tgaccttatg ctgctataag ttagattcta ggaggttaaa ttggcatgag tacatattct | 1440 |
| gaccatgcaa catattcata tataaccgat cgattcaggg aaaatgtcac tgagttaact | 1500 |
| taccctcccc atactggatt atctgtactc tctagtgctg gagacaaaat atgtatgtta | 1560 |
| aaaaataata agcacgtttt agcttttgca cacgagtgat atgtgttggt gataagatcc | 1620 |
| gaagttgata gagattgtgg cttgagtcac cgcaaaattt gatgacattt tctttagctg | 1680 |
| aaactacaag tacccatgcc ggtaatgaat tttattttaa aaaataatat gatatggctt | 1740 |
| aatgtagatc cattttttata tgttgtggat tatagaaaac catgctaatt acaactacga | 1800 |
| atttgaattt gaaatatcaa tagattccta caaaaatgta tatcactata cttttgctaa | 1860 |
| ttttctaaag atgttacaaa atttactgtt caaacccgac aaagaaggta gatgccaaat | 1920 |
| ctgtctaaaa gattatatta gatcgatcca cagattatag tatcaaagtg atggaaaaca | 1980 |

```
ttgtttgcac aaacaactga gtagctcgct acattttaga gctattttta catcattatt    2040
tactcttgac ttgttttatt gttctaaaat acccttctg agttcatgta tgaactatat    2100
atgaagcacc atctgttcat taagtaatga cccacttatg tgtgcatgtg atgacagacg    2160
ttgttccata accatgcttg catctagcta tgcatgtgat ttaaggttag ctgtccaatg    2220
tcttttgcaa ttctggaatc gggagaatat acttctatat atatatctta catttatcaa    2280
atagggagaa attaaatctt gatatcttga acgttgttca tcgtgaattt tgtcgttttg    2340
tatgcaatac taatatactt catctagtaa tacaaaaggt acaagaaaaa gaaaattgca    2400
cctggctatt tgtcttaata tattatgctg gaacatgaca ttgctatatg atacttcttt    2460
tgcag                                                                2465

<210> SEQ ID NO 14
<211> LENGTH: 20
<212> TYPE: DNA
<213> ORGANISM: Zea mays

<400> SEQUENCE: 14
gctcactctc gtcgcagcaa                                                  20

<210> SEQ ID NO 15
<211> LENGTH: 18
<212> TYPE: DNA
<213> ORGANISM: Zea mays

<400> SEQUENCE: 15
gatccggcgc agctgcac                                                    18

<210> SEQ ID NO 16
<211> LENGTH: 18
<212> TYPE: DNA
<213> ORGANISM: Zea mays

<400> SEQUENCE: 16
gaattaaacg gtattgag                                                    18

<210> SEQ ID NO 17
<211> LENGTH: 18
<212> TYPE: DNA
<213> ORGANISM: Zea mays

<400> SEQUENCE: 17
gatccggcgc agctgcac                                                    18

<210> SEQ ID NO 18
<211> LENGTH: 18
<212> TYPE: DNA
<213> ORGANISM: Zea mays

<400> SEQUENCE: 18
gaattaaacg gtattgag                                                    18

<210> SEQ ID NO 19
<211> LENGTH: 23
<212> TYPE: DNA
<213> ORGANISM: Zea mays

<400> SEQUENCE: 19
gtgttgtcat gactctacaa ggg                                              23
```

```
<210> SEQ ID NO 20
<211> LENGTH: 23
<212> TYPE: DNA
<213> ORGANISM: Zea mays

<400> SEQUENCE: 20
gagaattaaa cggtattgag tgg                                          23

<210> SEQ ID NO 21
<211> LENGTH: 23
<212> TYPE: DNA
<213> ORGANISM: Zea mays

<400> SEQUENCE: 21
gtccaatcaa aacacgacag cgg                                          23

<210> SEQ ID NO 22
<211> LENGTH: 23
<212> TYPE: DNA
<213> ORGANISM: Zea mays

<400> SEQUENCE: 22
gctcactctc gtcgcagcaa tgg                                          23

<210> SEQ ID NO 23
<211> LENGTH: 16
<212> TYPE: DNA
<213> ORGANISM: Zea mays

<400> SEQUENCE: 23
acgtaagcgc ttacgc                                                  16

<210> SEQ ID NO 24
<211> LENGTH: 121
<212> TYPE: DNA
<213> ORGANISM: Zea mays

<400> SEQUENCE: 24
ccgacggtct agctgcctcc acgccgctcc aaaaccccg cgtccaatca aaacacgaca    60
gcgggacgag cgaaaccacc gtggtttcgc caaaccgctt tccttcccat ctaaaaccgc  120
c                                                                 121

<210> SEQ ID NO 25
<211> LENGTH: 121
<212> TYPE: DNA
<213> ORGANISM: Zea mays

<400> SEQUENCE: 25
ccgacgtaag cgcttacgcc acgccgctcc aaaaccccg cgtccaatca aaacacgaca    60
gcgggacgag cgaaaccacc gtggtttcgc caaaccgctt tccttcccat ctaaaaccgc  120
c                                                                 121

<210> SEQ ID NO 26
<211> LENGTH: 121
<212> TYPE: DNA
<213> ORGANISM: Zea mays

<400> SEQUENCE: 26
ccgacggtct agctgcctcc acgccgctcc aaaaccccg cgtccaatca aaacacgaca    60
gcgggacgag cgaaacgtaa gcgcttacgc caaaccgctt tccttcccat ctaaaaccgc  120
```

| | |
|---|---:|
| c | 121 |

```
<210> SEQ ID NO 27
<211> LENGTH: 121
<212> TYPE: DNA
<213> ORGANISM: Zea mays

<400> SEQUENCE: 27
```

| | |
|---|---:|
| ccgacgtaag cgcttacgcc acgccgctcc aaaaccccg cgtccaatca aaacacgaca | 60 |
| gcgggacgag cgaaacgtaa gcgcttacgc caaaccgctt tccttcccat ctaaaaccgc | 120 |
| c | 121 |

```
<210> SEQ ID NO 28
<211> LENGTH: 121
<212> TYPE: DNA
<213> ORGANISM: Zea mays

<400> SEQUENCE: 28
```

| | |
|---|---:|
| ccgacggtct agctgcctcc acgccgctcc aaaaccccg cgtccaatca aaacacgaca | 60 |
| gcgggacgag cgaaacgtaa gcgcttacgc caaaccgctt tccttcccat ctataaccgc | 120 |
| c | 121 |

```
<210> SEQ ID NO 29
<211> LENGTH: 121
<212> TYPE: DNA
<213> ORGANISM: Zea mays

<400> SEQUENCE: 29
```

| | |
|---|---:|
| ccgacggtct agctgcctcc acgccgctcc aaaaccccg cgtccaatca aaacacgaca | 60 |
| gcgggacgag cgaaactcgg gagattccgc caaaccgctt tccttcccat ctaaaaccgc | 120 |
| c | 121 |

```
<210> SEQ ID NO 30
<211> LENGTH: 804
<212> TYPE: DNA
<213> ORGANISM: Zea mays

<400> SEQUENCE: 30
```

| | |
|---|---:|
| ctggtaatta ttggctgtag gattctaaac agagcctaaa tagctggaat agctctagcc | 60 |
| ctcaatccaa actaatgata tctatactta tgcaactcta aattttatt ctaaaagtaa | 120 |
| tatttcattt ttgtcaacga gattctctac tctattccac aatcttttga agctatattt | 180 |
| accttaaatc tgtactctat accaataatc atatattcta ttatttattt ttatctctct | 240 |
| cctaaggagc atccctctat gtctgcatgg cccccgcctc gggtcccaat ctcttgctct | 300 |
| gctagtagca cagaagaaaa cactagaaat gacttgcttg acttagagta tcagataaac | 360 |
| atcatgttta cttaacttta atttgtatcg gtttctacta tttttataat attttttgtct | 420 |
| ctatagatac tacgtgcaac agtataatca acctagttta atccagagcg aaggattttt | 480 |
| tactaagtac gtgactccat atgcacagcg ttccttttat ggttcctcac tgggcacagc | 540 |
| ataaacgaac cctgtccaat gttttcagcg cgaacaaaca gaaattccat cagcgaacaa | 600 |
| acaacataca tgcgagatga aaataaataa taaaaaaagc tccgtctcga taggccggca | 660 |
| cgaatcgaga gcctccatag ccagttttttt ccatcggaac ggcggttcgc gcacctaatt | 720 |
| atatgcacca cacgcctata aagccaacca acccgtcgga ggggcgcaag ccagacagaa | 780 |

```
gacagcccgt cagcccctct cgtt                                     804
```

<210> SEQ ID NO 31
<211> LENGTH: 896
<212> TYPE: DNA
<213> ORGANISM: Zea mays

<400> SEQUENCE: 31

```
gtgcagcgtg acccggtcgt gcccctctct agagataatg agcattgcat gtctaagtta   60
taaaaaatta ccacatattt tttttgtcac acttgtttga agtgcagttt atctatcttt  120
atacatatat ttaaacttta ctctacgaat aatataatct atagtactac aataatatca  180
gtgttttaga gaatcatata aatgaacagt tagacatggt ctaaaggaca attgagtatt  240
ttgacaacag gactctacag ttttatcttt ttagtgtgca tgtgttctcc ttttttttg   300
caaatagctt cacctatata atacttcatc cattttatta gtacatccat ttagggttta  360
gggttaatgg ttttttataga ctaatttttt tagtacatct attttattct attttagcct  420
ctaaattaag aaaactaaaa ctctatttta gtttttttat ttaataattt agatataaaa  480
tagaataaaa taaagtgact aaaaattaaa caaatcccct ttaagaaatt aaaaaaacta  540
aggaaacatt tttcttgttt cgagtagata atgccagcct gttaaacgcc gtcgacgagt  600
ctaacggaca ccaaccagcg aaccagcagc gtcgcgtcgg gccaagcgaa gcagacggca  660
cggcatctct gtcgctgcct ctggacccct ctcgagagtt ccgctccacc gttggacttg  720
ctccgctgtc ggcatccaga aattgcgtgg cggagcggca gacgtgagcc ggcacggcag  780
gcggcctcct cctcctctca cggcaccggc agctacgggg gattcctttc ccaccgctcc  840
ttcgctttcc cttcctcgcc cgccgtaata aatagacacc ccctccacac cctctt       896
```

<210> SEQ ID NO 32
<211> LENGTH: 1462
<212> TYPE: DNA
<213> ORGANISM: Zea mays

<400> SEQUENCE: 32

```
ggctggtatc gataaatgtt tccacataga ttttgcatat cataatgatg tttgtcgttc   60
cgtatctatg tttcatacaa aatttttacg catatcgcaa cacatgggca catacctagt  120
gactgtataa ctctgcatgt atgagtgtat gactatatga tgtagtaact aataagaagg  180
gtagacattt gagtgattct tttattcctg gacttgtaag acttgacatt tctgccttga  240
gtgcgataca tcatatggac aggggttatg catacactgc ttgtttgttg tttatgttct  300
aagagcatct ccaacaacgt gacatatgaa aatgccctac aatttaaaaa tggttatatt  360
ttataaaatt tagggcataa ataaaacatc ccgctccaac attaaagcct taaatctatt  420
atagggaagc ccactatgat atagtatatt tgaggcactt tagagggtgc cctataattt  480
tttgaccatt tttttatgaa atgagacact attggagtat ttttttttccg tagagcacca  540
tatttcaatt tgagacacca atttaaggca ttgttggaga tgttctaaat gttggtttat  600
tttgtctgta tcgttgtggt tttgatagtg gtgcctttgc aatgtacatc ttacattgac  660
aataataata ggtaaaactc tacaattttt ttatctaatg gactcttgta tgaaacattg  720
tacttgcaca catctgatgt aaacactgca tactttttaac agtgacaaga ttctgtttca  780
ttttagggct agtttgggaa ccaaatttta ttagggtttt tattttctaa gaaaagtaa   840
tttattttac cttgagaaaa tataaattac ttgagaaaat agagttccaa actagctctt  900
atctttgtcg aatcctcctc tattcaaatg tgacatttct ggcacgtgac aactggtgat  960
```

```
gttgtagacc gtgttaagta atacgtgtca ttattactaa atgccatttt agtaaatgtt    1020
gagtatgtac tctactacag taagtattat tggtgtattt acactagaca gttggcggcc    1080
tggcgggtaa agttatcctg tagaaagttg ggccaggcca aaaccaaccg ccaaaggaaa    1140
ggccttccgg cccgcccacc tttgcgcgcc gaaggtcagt tccttcagtc tcctcccgct    1200
tcagactctg accacgtcga caatccgggc cgaaacacat ctgcaccgtc cacttgcgac    1260
agattgaaca caccacttct atccacgtca gcgatccgtg gcactagccc ttccaccaat    1320
cagcccaagt tgccccttc ctttaaattc gccgcaccca tgctcttct cacggccata    1380 gaaatcgacc gagcgaatcc ctcgcatcgc attcgcagcc tttgctgcat cacaccaccg    1440
cgaaacccca gcagccgcat ct                                           1462

<210> SEQ ID NO 33
<211> LENGTH: 535
<212> TYPE: DNA
<213> ORGANISM: Zea mays

<400> SEQUENCE: 33
gtccgccttg tttctcctct gtctcttgat ctgactaatc ttggtttatg attcgttgag      60
taattttggg gaaagcttcg tccacagttt tttttcgatg aacagtgccg cagtggcgct     120
gatcttgtat gctatcctgc aatcgtggtg aacttattc ttttatatcc tttactccca     180
tgaaaaggct agtaatcttt ctcgatgtaa catcgtccag cactgctatt accgtgtggt     240
ccatccgaca gtctggctga acacatcata cgatctatgg agcaaaaatc tatcttccct     300 gttcttaat gaaggacgtc attttcatta gtatgatcta ggaatgttgc aacttgcaag     360
gaggcgtttc tttctttgaa tttaactaac tcgttgagtg gccctgtttc tcggacgtaa     420
ggcctttgct gctccacaca tgtccattcg aattttaccg tgtttagcaa gggcgaaaag     480
tttgcatctt gatgatttag cttgactatg cgattgcttt cctggacccg tgcag         535

<210> SEQ ID NO 34
<211> LENGTH: 1013
<212> TYPE: DNA
<213> ORGANISM: Zea mays

<400> SEQUENCE: 34
gtacgccgct cgtcctcccc cccccccctc tctaccttct ctagatcggc gttccggtcc      60
atgcatggtt agggcccggt agttctactt ctgttcatgt ttgtgttaga tccgtgtttg     120
tgttagatcc gtgctgctag cgttcgtaca cggatgcgac ctgtacgtca gacacgttct     180
gattgctaac ttgccagtgt ttctctttgg ggaatcctgg gatggctcta gccgttccgc     240
agacgggatc gatttcatga tttttttgt ttcgttgcat agggtttggt ttgcccttt     300 cctttatttc aatatatgcc gtgcacttgt ttgtcgggtc atcttttcat gctttttttt     360
gtcttggttg tgatgatgtg gtctggttgg gcggtcgttc tagatcggag tagaattctg     420
tttcaaacta cctggtggat ttattaattt tggatctgta tgtgtgtgcc atacatattc     480
atagttacga attgaagatg atggatggaa atatcgatct aggataggta tacatgttga     540
tgcgggtttt actgatgcat atacagagat gcttttttgtt cgcttggttg tgatgatgtg     600
gtgtggttgg gcggtcgttc attcgttcta gatcggagta gaatactgtt tcaaactacc     660
tggtgtattt attaattttg gaactgtatg tgtgtgtcat acatcttcat agttacgagt     720
ttaagatgga tggaaatatc gatctaggat aggtatacat gttgatgtgg gttttactga     780
```

| | | |
|---|---|---|
| tgcatataca tgatggcata tgcagcatct attcatatgc tctaaccttg agtacctatc | 840 | |
| tattataata aacaagtatg ttttataatt attttgatct tgatatactt ggatgatggc | 900 | |
| atatgcagca gctatatgtg gattttttta gccctgcctt catacgctat ttatttgctt | 960 | |
| ggtactgttt cttttgtcga tgctcaccct gttgtttggt gttacttctg cag | 1013 | |

```
<210> SEQ ID NO 35
<211> LENGTH: 1329
<212> TYPE: DNA
<213> ORGANISM: Zea mays

<400> SEQUENCE: 35
```

| | | |
|---|---|---|
| gtaactgcga tcatccatcc tcccgcttcc actctcccct cacctcctct gcttgctagg | 60 | |
| tatacgaaca tacgatttat tacgggttat atgggggctt cgattcccag atctggcgat | 120 | |
| ctattatcgt agctccgagt cctcgatcta gtaattgtgg gatatgcttg taagaggctc | 180 | |
| tgagatgggt tgggttgggt tgggtcgctg tgacgattcc aacagcctcg tttcttaggg | 240 | |
| ttggatcttc tcgtggtttc cttttaatt aaataagtac ctgatgcaga atggtgcgtc | 300 | |
| ctattagatg gaaccttgat cttgatgcat ctaaccttga tcttgttcgc tgtgatgatt | 360 | |
| ccaacaggct cgtttcttag gcctgttcgt ctggttcgtc agatcagttt cgttgctttt | 420 | |
| ggcctcgttg taaggtccat ccagatcgga gtagaatcga atgatttatt atacggtagc | 480 | |
| tgctggtctc attagatttg gatctgcatg ggttgaacat atgtattcat aattaatatg | 540 | |
| gtgtatacgt actagtttgc tggtcttatt ttttagcct gattgcttct gcctttctgg | 600 | |
| caacgcctga tccacgcgtt agctagagtg gattttagtt cctgtttac gcggccacac | 660 | |
| ctgccgccta gaaaagctgc agcgagaact ctaattaaat ttggatctac atgtgctagc | 720 | |
| atatatgttt gtaattaata tgatggatga atatgtgctt cagagttgag ttcctgttga | 780 | |
| tgctgtagtt ctgcctgaat tgttgaggct gtagcttctg cctgattaaa atgcaccgtg | 840 | |
| cctatctgtt aaactctagg gtgtgtgatt tagccggtga cggtggttta atatgtgtaa | 900 | |
| tttcactgct tatagtaatg caattcacct ttgcttgaac atgcattgtc ttgttgctttt | 960 | |
| gttctataca catgcttagc tattatctga tgagcatgca ctgttttgtt ctgtttgata | 1020 | |
| tgcatgctca gaaatatgta gatgtgtggc tcctgctcgg ttgttctttta tcatccacct | 1080 | |
| gttgaacatg catgttcttg tcgcttatct ttattatata ttaccttcgt tctcgaatat | 1140 | |
| ttgtcgcccg ctagttcatt tttgaactaa accgtgacaa ataaaataga acgtagggag | 1200 | |
| tggcatcatg ctgctactgt accttacggt ggcaactaca tcttgagcac gcatatatct | 1260 | |
| tatagtgttc cttttctttt cctccttggt ctactgttat atgcttacct tttttggtt | 1320 | |
| tccttgcag | 1329 | |

```
<210> SEQ ID NO 36
<211> LENGTH: 893
<212> TYPE: DNA
<213> ORGANISM: Zea mays

<400> SEQUENCE: 36
```

| | | |
|---|---|---|
| gtgagcgcag tccccttcc cctccttcca attcaattcg tcttctcgtt cgcagcccta | 60 | |
| ggatttgggg gtctggaggg gtttgatcgt ttctcgccgt gaatctgctt tggtgtaaac | 120 | |
| caacggatct cggatcgtag tcttcagaag atcccggatt ttgcggtttg gcccctcctg | 180 | |
| gattcaattc gtcgtatcgt tcgcagccct aggatttggg gatctggagg ggtttgatcg | 240 | |
| tttctcgccg cgaatctgct ctggtgtaaa ccaacggatc tcgggtcgta gtcttcagaa | 300 | |

```
ggtcccggat tttgcggttt ggcccctcct ggattcaatt cgtcgtatcg ttcgcagccc    360
taggatttgg ggatctggag gggtttgatc ctttctcgcc gcgaatctgc tctggtataa    420
ccaacggatc tcgggtcgta gtcttcagaa ggtcccggat tttgcggttt ggtggttctt    480
gctctatgaa tcagagggat ggttcttccc ggatttatgc cttgcggcca ctctgtcgaa    540
tcatggggtt tcgacccgat tcgtaggcgt gctccctgtt ttggatggga agtaggcgtg    600
tttgtagtat tcgtgcttcg attcgtcaac ggagattaga agacctggga tgggatttga    660
ggaaatctag gtatctgtct agcacgtttc tagatctatt cttcagctgt tatatgagag    720
taattttgga accctggtgg ggtatgtttg accgagtatt ctgtagatta ttgtccgtga    780
cttgctggct gttaccgtcc ttatctctgc atcatctatc tgtgctagtt tctgcgtgct    840
tctcaaatat ttccggcctg tgtagcatgt gactgataat atgattttgg cag           893
```

<210> SEQ ID NO 37
<211> LENGTH: 856
<212> TYPE: DNA
<213> ORGANISM: Zea mays

<400> SEQUENCE: 37

```
gtaaggttcc cttccctcct cccctcacac ccctgttcgt gttccttcgg atcggatctc     60
agtggtgatg ttagacgtcc gcggctgcct acgtagtggc attgccgccc gaaaggtttg    120
tttaggtggg gtagatccga acaggccgg  atctggacca tgtccgcggc ggggcggcgg    180
gacttgatcg cgtagctgtc gtgtgcattt ctccctacca gtggcggaat cggcgatgtg    240
gacctaaggg ctaaggctta tctgctgcct tgaccatttc gtcgctgaca aaaacaaagt    300
gacaatcatg ccgttctctg tttgtttatc tggatcgtta ttacgctgtg aatcctgcga    360
tatgtggcta agtgattttt cttctttttc tgggggcagt ttagcctttg acccagtcct    420
aggtgtggtc actaggactg tgtagcatga tgagtgaggt tgcagcaggc tgattgctag    480
tggacgtttt tttccccaat tgttaggtt  ttcacgctcc aggttgtgca agtaattttg    540
ctagtgattg tgtgatccat cttcaacgtt gaaccttgtt tttccccta aaaccccaa     600 caggaaatct tgccccgact tctattgcaa aaattgtaac gcttagcacc ctgattgact    660
caattcctgt cactaggcat gctcggtcaa aagcagatga tttaccactt agaaactgcc    720
ctgcccctgc tttccacata gcatttcgaa cttttttgact actattgaca ccccctaac    780 ttgccgaact atttctctct tcagctacta tttacctagt tataattaca taaatgtttg    840
tgtgtatctt gtgcag                                                     856
```

<210> SEQ ID NO 38
<211> LENGTH: 1026
<212> TYPE: DNA
<213> ORGANISM: Zea mays

<400> SEQUENCE: 38

```
gtatgcttgc tgccttgctc tcctgttcat ctccgtgcta aacctctgtc ctctgggtgg     60
gtttttgctg ggattttgag ctaatctgct ggtcccggta gaaaagatca tgtcccctga    120
gcagctcaag cgctcgcctt agccgcgtcc ttgccccccg ccattttttg cggtttcggt    180
gtgttcccgt gactcgccgg gtgcgtcatc gcctgaatct tgtctgggct ctgctgacat    240
gttcttggct agtgggtttt atagattcct ctgatctaaa ccgtgcctgt gctgcgcaca    300
gaactctccc ctgtcctttc ctggggtttt ggttacgtgg tggtagtaag cttggatttg    360
```

-continued

```
cacatggata aagttgttct aagctccgtg ggttgcttga catcttgctg ttattgcgtg        420
ccgtgctcac tttttttgca atccgaggaa tgaatttgtc gtttactcgt tttggtggat        480
tattagcgcg aaaaaaaaac tctttttttt ttgttctttt actacgaaaa gcatcttctt        540
ggattttgct atcttctttt actacgaaaa actcttgagt ctaggaattt gaatttgtga        600
tgtccattct tgcagtgcgc tgtgctttat tgggaagcca aatcctatta ttttctgcct        660
ctagggtctg aatggaatca gtactcttga gacagaaaat caatccaatc aagttgattt        720
ctttctttaa aaatattatc acagaactaa gtgcttgtgc ggaatcagta ctggcttttg        780
tttggtggag gatcaatact tgcttttgtt tgggggtggc aactgttttg ctataagatt        840
ccatgtgttc ctgttgagat gaatcatata tagtatagct gcatactaca aatctgtttt        900
tcaaatttag gttgctttgg catgatctat tttttttgtca gacagacttt ctaagtggta        960
gctcttgatt tcttgttctt gtacaactgg tgctgctgaa tcttgaccgt atagctcgaa       1020
ttgcag                                                                  1026
```

IMPROVING AGRONOMIC CHARACTERISTICS IN MAIZE BY MODIFICATION OF ENDOGENOUS MADS BOX TRANSCRIPTION FACTORS

REFERENCE TO SEQUENCE LISTING SUBMITTED ELECTRONICALLY

The official copy of the sequence listing is submitted electronically via EFS-Web as an ASCII formatted sequence listing with a file named 7847 ST25.txt created on Mar. 3, 2019 and having a size of 51 kilobytes and is filed concurrently with the specification. The sequence listing comprised in this ASCII formatted document is part of the specification and is herein incorporated by reference in its entirety.

FIELD

This disclosure relates to compositions and methods for improving yield in plants.

BACKGROUND

Global demand and consumption of agricultural crops is increasing at a rapid pace. Accordingly, there is a need to develop new compositions and methods to increase yield in plants. This invention provides such compositions and methods.

SUMMARY

A guide polynucleotide molecule that targets an endogenous genomic locus of a plant cell (e.g., maize), wherein the genomic locus comprises a polynucleotide that encodes a polypeptide comprising an amino acid sequence that is at least 80%, 85%, 90%, 95% or 99% identical to an amino acid sequence selected from the group consisting of SEQ ID NOS: 1-4. In an embodiment, the guide polynucleotide targets a regulatory region of the polynucleotide. A plant cell that includes these guide polynucleotides are provided wherein the guide polynucleotide interacts with a Cas endonuclease at the endogenous genomic locus. In an embodiment, the guide polynucleotide targets a regulatory region of the endogenous genomic loci having a genomic sequence that is at least 90% identical to a sequence selected from the group consisting of SEQ ID NOS: 5-6. In an embodiment, the endogenous genomic locus comprises a regulatory region of the polynucleotide encoding the polypeptide, wherein the regulatory region comprises a polynucleotide sequence that is at least 90% identical to one of SEQ ID NOS: 5-6.

A plant cell includes a targeted genetic modification at a genomic locus that encodes a polypeptide comprising an amino acid sequence that is at least 90% identical to an amino acid sequence selected from the group consisting of SEQ ID NOS: 1-4, wherein the targeted genetic modification modulates the expression level and/or activity of the encoded polypeptide. In an embodiment, the targeted modification results in an increased expression level of the polynucleotide. In an embodiment, the targeted genetic modification is selected from the group consisting of an insertion, deletion, single nucleotide polymorphism (SNP), and a polynucleotide modification. In an embodiment, the targeted genetic modification is present in (a) the coding region; (b) a non-coding region; (c) a regulatory sequence; (d) an untranslated region; or (e) any combination of (a)-(d) of the genomic locus that encodes the polypeptide. In an embodiment, the plant cell is from a monocot plant. In an embodiment, the monocot plant is maize. In an embodiment, the targeted modification is an insertion of a regulatory element at the genomic locus, wherein the genomic locus comprises a polynucleotide sequence that is at least 90% identical to one of SEQ ID NOS: 5-6. In an embodiment, the regulatory element is a heterologous promoter. In an embodiment, the heterologous promoter is a moderately constitutive promoter. In an embodiment, the regulatory element is an enhancer element.

A plant comprising a targeted genetic modification at a genomic locus that encodes a polypeptide comprising an amino acid sequence that is at least 95% identical to an amino acid sequence selected from the group consisting of SEQ ID NOS: 1-4, wherein the targeted genetic modification modulates the expression level and/or activity of the encoded polypeptide compared to a control plant not comprising the genetic modification. In an embodiment, the plant is maize. In an embodiment, the plant exhibits increased expression of a polynucleotide that encodes a polypeptide that is at least 95% identical to an amino acid sequence selected from the group consisting of SEQ ID NO: 1 or 2, when compared to the control plant. In an embodiment, the plant is a maize plant and the maize plant exhibits increased grain yield.

A maize seed comprising a targeted genetic modification at a genomic locus that encodes a polypeptide comprising an amino acid sequence that is at least 95% identical to an amino acid sequence selected from the group consisting of SEQ ID NOS: 1-4, wherein the targeted genetic modification modulates the expression level and/or activity of the encoded polypeptide. In an embodiment, the targeted modification in the maize seed results in increased expression level of a polynucleotide encoding a polypeptide comprising an amino acid sequence that is at least 95% identical to SEQ ID NO: 1, either in the seed and/or the plant. In an embodiment, the maize seed further comprises a polypeptide encoding herbicide tolerance and/or insect resistance. In an embodiment, the targeted modification comprises insertion in or replacement of the endogenous regulatory element with a heterologous regulatory element of ZmGOS2 promoter.

A method for increasing grain yield in a maize plant, the method comprising introducing in a regenerable maize plant cell a targeted genetic modification at a genomic locus that encodes a polypeptide comprising an amino acid sequence that is at least 90% identical to an amino acid sequence selected from the group consisting of SEQ ID NOS: 1-4; and generating the plant, wherein the level and/or activity of the encoded polypeptide is modulated in the plant when compared to a control plant not comprising the genetic modification. In an embodiment, the targeted genetic modification is introduced using a genome modification technique selected from the group consisting of a polynucleotide-guided endonuclease, CRISPR-Cas endonucleases, targeted base editing deaminases, a zinc finger nuclease, a transcription activator-like effector nuclease (TALEN), engineered site-specific meganucleases, or Argonaute. In an embodiment, the targeted genetic modification is present in (a) the coding region; (b) a non-coding region; (c) a regulatory sequence; (d) an untranslated region; or (e) any combination of (a)-(d) of the genomic locus that encodes the polypeptide.

A method for increasing photosynthetic activity in a maize plant, the method comprising introducing in a regenerable plant cell a targeted genetic modification at a genomic locus that encodes a polypeptide comprising an amino acid sequence that is at least 90% identical to an amino acid sequence selected from the group consisting of SEQ ID NOS: 1-4; and generating the plant, wherein the level and/or activity of the encoded polypeptide is increased in the maize plant. In an embodiment, the method includes polynucleotide encodes a polypeptide comprising an amino acid sequence that is at least 95% identical to an amino acid sequence selected from the group consisting of SEQ ID NO: 1. In an embodiment, the targeted modification results in an integration of a heterologous plant derived enhancer element such that the expression level of the polynucleotide is increased.

A method of introducing a site-directed modification at a genomic locus to increase expression level of a polynucleotide, the method comprising introducing in a regenerable plant cell (e.g., maize) a targeted genetic modification at the genomic locus that encodes a polypeptide comprising an amino acid sequence that is at least 90% identical to an amino acid sequence selected from the group consisting of SEQ ID NOS: 1-4; and obtaining the plant, wherein the expression level of the encoded polypeptide is increased compared to a control plant. In an embodiment, the targeted modification is swapping an endogenous promoter element at the genomic locus with a heterologous regulatory element such that the heterologous regulatory element increases the expression level of the polynucleotide.

A method of identifying a genomic variation in a genomic region of a plant, the method comprising performing genotyping of one or more isolated polynucleotide samples of one or more maize lines, the polynucleotide samples comprising a portion of the polynucleotide of the genomic region that encodes a polypeptide comprising an amino acid sequence that is at least 95% identical to SEQ ID NO: 1 and identifying the genomic variation based on the genotyping. In an embodiment, the maize lines are inbreds. In an embodiment, the maize lines are from a tropical or subtropical germplasm source. In an embodiment, the genomic variation is in a coding region of the genomic region that encodes the polypeptide. In an embodiment, the genomic variation is in a non-coding region. In an embodiment, the genomic variation results in a haplotype that increases the expression of the polynucleotide encoding the polypeptide.

Also provided are recombinant DNA constructs comprising a regulatory element operably linked to a polynucleotide encoding a polypeptide comprising an amino acid sequence that is at least 80% identical to an amino acid sequence selected from the group consisting of SEQ ID NOS: 1-4. In certain embodiments the regulatory element is a heterologous promoter, such as for example, GOS2 moderately constitutive promoter.

Further provided are plant cells, plants, and seeds comprising a targeted genetic modification at a genomic locus that encodes a polypeptide comprising an amino acid sequence that is at least 80% identical to an amino acid sequence selected from the group consisting of SEQ ID NOS: 1-4, wherein the genetic modification increases the level and/or activity of the encoded polypeptide. In certain embodiments, the genetic modification is selected from the group consisting of an insertion, deletion, single nucleotide polymorphism (SNP), and a polynucleotide modification. In certain embodiments the targeted genetic modification is present in (a) the coding region; (b) a non-coding region; (c) a regulatory sequence; (d) an untranslated region; or (e) any combination of (a)-(d) of the genomic locus that encodes the polypeptide.

Provided are methods for increasing yield in a plant by expressing in a regenerable plant cell a recombinant DNA construct comprising a regulatory element operably linked to a polynucleotide encoding a polypeptide comprising an amino acid sequence that is at least 80% identical to an amino acid sequence selected from the group consisting of SEQ ID NOS: 1-4; and generating the plant, wherein the plant comprises in its genome the recombinant DNA construct. In certain embodiments, the regulatory element is a heterologous promoter. In certain embodiments, the plant is a monocot plant. In certain embodiments, the monocot plant is maize. In certain embodiments, the yield is grain yield.

Further provided are methods for increasing yield in a plant by introducing in a regenerable plant cell a targeted genetic modification at a genomic locus that encodes a polypeptide comprising an amino acid sequence that is at least 80% identical to an amino acid sequence selected from the group consisting of SEQ ID NOS: 1-4; and generating the plant, wherein the level and/or activity of the encoded polypeptide is increased in the plant. In certain embodiments, the genetic modification is introduced using a genome modification technique selected from the group consisting of a polynucleotide-guided endonuclease, CRISPR-Cas endonucleases, base editing deaminases, a zinc finger nuclease, a transcription activator-like effector nuclease (TALEN), an engineered site-specific meganuclease, or an Argonaute. In certain embodiments, the targeted genetic modification is present in (a) the coding region; (b) a non-coding region; (c) a regulatory sequence; (d) an untranslated region; or (e) any combination of (a)-(d) of the genomic locus that encodes the polypeptide. In certain embodiments, the plant cell is from a monocot plant. In certain embodiments, the monocot plant is maize. In certain embodiments, the yield is grain yield.

Provided are methods for increasing photosynthetic activity in a plant by expressing in a regenerable plant cell a recombinant DNA construct comprising a regulatory element operably linked to a polynucleotide encoding a polypeptide comprising an amino acid sequence that is at least 80% identical to an amino acid sequence selected from the group consisting of SEQ ID NOS: 1-4; and generating the plant, wherein the plant comprises in its genome the recombinant DNA construct.

Also provided are methods for increasing photosynthetic activity in a plant by introducing in a regenerable plant cell a targeted genetic modification at a genomic locus that encodes a polypeptide comprising an amino acid sequence that is at least 80% identical to an amino acid sequence selected from the group consisting of SEQ ID NOS: 1-4; and generating the plant, wherein the level and/or activity of the encoded polypeptide is increased in the plant. In certain embodiments, the genetic modification is introduced using a genome modification technique selected from the group consisting of a polynucleotide-guided endonuclease, CRISPR-Cas endonucleases, base editing deaminases, a zinc finger nuclease, a transcription activator-like effector nuclease (TALEN), an engineered site-specific meganucleases, or an Argonaute. In certain embodiments, the targeted genetic modification is present in (a) the coding region; (b) a non-coding region; (c) a regulatory sequence; (d) an untranslated region; or (e) any combination of (a)-(d) of the genomic locus that encodes the polypeptide. In certain embodiments, the plant cell is from a monocot plant. In certain embodiments, the monocot plant is maize.

BRIEF DESCRIPTION OF THE DRAWINGS AND SEQUENCE LISTING

FIG. 1 is a schematic illustration representing the locations and approaches towards replacing the endogenous promoter region of the genomic locus encoding SEQ ID NO:

1 (Line E) through homologous recombination mediated genome editing with the maize GOS2 promoter with UBI1ZM INTRON1 replacement. CR indicates CRISPR recognition sites for Cas9-mediated genome editing. Note that the illustration is not drawn to scale.

FIG. 2 is a schematic illustration representing the locations and approaches towards inserting a heterologous maize promoter into the endogenous promoter region of the genomic locus encoding SEQ ID NO: 1 (Line E) through homologous recombination mediated genome editing with the maize ZM-EIF5C PRO:ADH1 INTRON insertion. CR indicates CRISPR recognition sites for Cas9-mediated genome editing. Note that the illustration is not drawn to scale.

FIG. 3 is a schematic illustration representing the locations and approaches towards inserting a heterologous maize promoter into the endogenous promoter region of the genomic locus encoding SEQ ID NO: 1 (Line E) through homologous recombination mediated genome editing with the maize GOS2 promoter with UBI1ZM INTRON1 insertion. CR indicates CRISPR recognition sites for Cas9-mediated genome editing. Note that the illustration is not drawn to scale.

Figure 1:
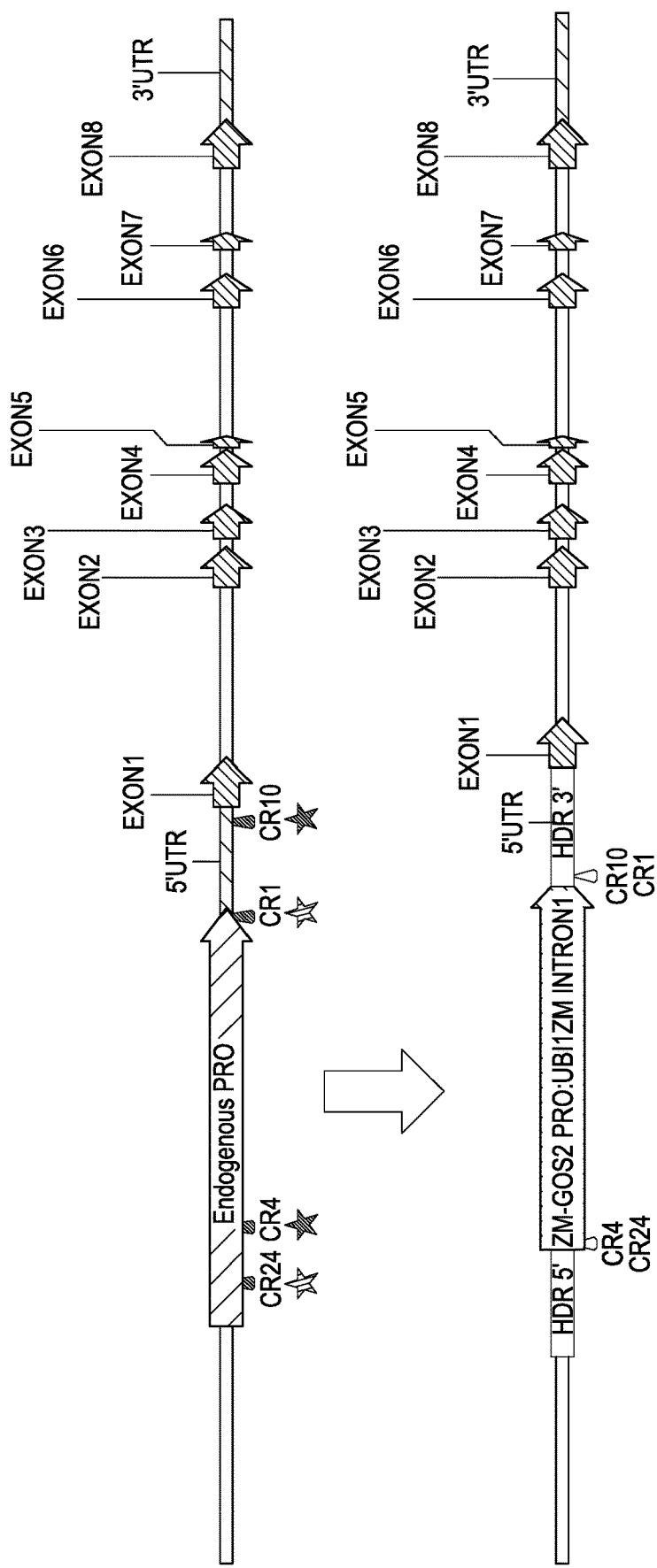

The disclosure can be more fully understood from the following detailed description and the accompanying drawings and Sequence Listing, which form a part of this application.

The sequence descriptions and sequence listing attached hereto comply with the rules governing nucleotide and amino acid sequence disclosures in patent applications as set forth in 37 C.F.R. §§ 1.821 and 1.825. The sequence descriptions comprise the three letter codes for amino acids as defined in 37 C.F.R. §§ 1.821 and 1.825, which are incorporated herein by reference.

TABLE 1

| Sequence Listing | |
|---|---|
| SEQ ID NOS | DESCRIPTION |
| SEQ ID NO: 1 | ZMM28 polypeptide B73 |
| SEQ ID NO: 2 | ZMM28 polypeptide MO17 |
| SEQ ID NO: 3 | ZMM28 (ALT1) |
| SEQ ID NO: 4 | ZmMADS27 (MOD) |
| SEQ ID NO: 5 | Zmm28 Promoter (5' to 3')-Line G |
| SEQ ID NO: 6 | Zmm28 Promoter (5' to 3')-Line E |
| SEQ ID NO: 7 | Zmm28 Promoter (5' to 3')-B73 |
| SEQ ID NO: 8 | Zmm28 intron B73 |
| SEQ ID NO: 9 | Zmm28 intron MO17 |
| SEQ ID NO: 10 | Zmm28 intron Line H9 |
| SEQ ID NO: 11 | Zmm28 intron Line H11 |
| SEQ ID NO: 12 | Zmm28 intron Line G |
| SEQ ID NO: 13 | Zmm28 intron Line E |
| SEQ ID NO: 14 | ZMM28-CR10 (Line G) target site |
| SEQ ID NO: 15 | ZMM28-CR11 (Line G) target site |
| SEQ ID NO: 16 | ZMM28-CR4 (Line G) target site |
| SEQ ID NO: 17 | ZMM28-CR11 (Line G) target site |
| SEQ ID NO: 18 | ZMM28-CR4 (Line G) target site |
| SEQ ID NO: 19 | ZMM28-CR24 (Line E) target site |
| SEQ ID NO: 20 | ZMM28-CR4 (Line E) target site |
| SEQ ID NO: 21 | ZMM28-CR1 (Line E) target site |
| SEQ ID NO: 22 | ZMM28-CR10 (Line E) target site |
| SEQ ID NO: 23 | Zm-AS2 EME 16-bp |

TABLE 1-continued

| Sequence Listing | |
|---|---|
| SEQ ID NOS | DESCRIPTION |
| SEQ ID NO: 24 | EE1275 – EME variation + promoter region |
| SEQ ID NO: 25 | EE1534 – EME variation + promoter region |
| SEQ ID NO: 26 | EE1535 – EME variation + promoter region |
| SEQ ID NO: 27 | EE1536 – EME variation + promoter region |
| SEQ ID NO: 28 | EE1785 (similar to EE1535, but includes other optimizations) |
| SEQ ID NO: 29 | EE1845 (similar to EE1535 – "null" enhancer) |
| SEQ ID NO: 30 | ZM-GOS2 PRO |
| SEQ ID NO: 31 | UBI1ZM PRO |
| SEQ ID NO: 32 | Zm-H2B PRO |
| SEQ ID NO: 33 | ADH1 INTRON1 |
| SEQ ID NO: 34 | UBI1ZM INTRON1 |
| SEQ ID NO: 35 | ZM-UBI LV5 INTRON1 |
| SEQ ID NO: 36 | ZM-GOS2 INTRON1 |
| SEQ ID NO: 37 | ZM-HPLV9 INTRON1 |
| SEQ ID NO: 38 | ZM-SH1 INTRON1 |

I. COMPOSITIONS

A. Polynucleotides and Polypeptides

The present disclosure provides polynucleotides encoding polypeptides. Accordingly, as used herein "polypeptide," "protein," or the like, refers to a protein represented by a SEQ ID NO.

One aspect of the disclosure provides a polynucleotide encoding a polypeptide comprising an amino acid sequence that is at least 80-99%% identical to the amino acid sequence of any one of SEQ ID NOS: 1-4).

Phylogenetic analysis of ZMM28 (Zm00001d022088) with the AP1-FUL clade MADS-box genes from *Arabidopsis*, rice, sorghum, barley, Brachypodium and maize is shown in FIG. 1b. ZMM28 clusters with and shares 94%, 75%, 69%, and 76% amino acid sequence identity with sorghum Sb02g038780.1, barley AK361063 and AK361227, and rice LOC_Os07g41370.1 (OsMADS18) proteins, respectively.

As used herein "encoding," "encoded," or the like, with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal and fungal mitochondria, the bacterium *Mycoplasma capricolum* (Yamao, et al., (1985) Proc. Natl. Acad. Sci. USA 82:2306-9) or the ciliate Macronucleus, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray, et al., (1989) Nucleic Acids Res. 17:477-98).

As used herein, "polynucleotide" includes reference to a deoxyribopolynucleotide, ribopolynucleotide or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The terms "polypeptide," "peptide" and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers.

As used herein, "sequence identity" or "identity" in the context of two nucleic acid or polypeptide sequences includes reference to the residues in the two sequences, which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences, which differ by such conservative substitutions, are said to have "sequence similarity" or "similarity." Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, (1988) Computer Applic. Biol. Sci. 4:11-17, e.g., as implemented in the program PC/GENE (Intelligenetics, Mountain View, California, USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence or the complete cDNA or gene sequence.

As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well known in the art. The local homology algorithm (BESTFIT) of Smith and Waterman, (1981) Adv. Appl. Math 2:482, may conduct optimal alignment of sequences for comparison; by the homology alignment algorithm (GAP) of Needleman and Wunsch, (1970) J. Mol. Biol. 48:443-53; by the search for similarity method (Tfasta and Fasta) of Pearson and Lipman, (1988) Proc. Natl. Acad. Sci. USA 85:2444; by computerized implementations of these algorithms, including, but not limited to: CLUSTAL in the PC/Gene program by Intelligenetics, Mountain View, California, GAP, BESTFIT, BLAST, FASTA and TFASTA in the Wisconsin Genetics Software Package®, Version 8 (available from Genetics Computer Group (GCG® programs (Accelrys, Inc., San Diego, CA)). The CLUSTAL program is well described by Higgins and Sharp, (1988) Gene 73:237 44; Higgins and Sharp, (1989) CABIOS 5:151 3; Corpet, et al., (1988) Nucleic Acids Res. 16:10881-90; Huang, et al., (1992) Computer Applications in the Biosciences 8:155-65, and Pearson, et al., (1994) Meth. Mol. Biol. 24:307-31. The preferred program to use for optimal global alignment of multiple sequences is PileUp (Feng and Doolittle, (1987) J. Mol. Evol., 25:351-60 which is similar to the method described by Higgins and Sharp, (1989) CABIOS 5:151-53 and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, CURRENT PROTOCOLS IN MOLECULAR BIOLOGY, Chapter 19, Ausubel, et al., eds., Greene Publishing and Wiley-Interscience, New York (1995).

GAP uses the algorithm of Needleman and Wunsch, supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package® are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package® is BLOSUM62 (see, Henikoff and Henikoff, (1989) Proc. Natl. Acad. Sci. USA 89:10915).

Unless otherwise stated, sequence identity/similarity values provided herein refer to the value obtained using the BLAST 2.0 suite of programs using default parameters (Altschul, et al., (1997) Nucleic Acids Res. 25:3389-402).

As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (Claverie and States, (1993) Comput. Chem. 17:191-201) low-complexity filters can be employed alone or in combination.

Accordingly, in any of the embodiments described herein, the polynucleotide may encode a polypeptide that is at least 80% identical to any one of SEQ ID NOS: 1-4. For example, the polynucleotide may encode a polypeptide that is at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, or at least 99% identical to the amino acid sequence of any one of SEQ ID NOS: 1-4.

B. Recombinant DNA Construct

Also provided is a recombinant DNA construct comprising any of the polynucleotides described herein. In certain embodiments, the recombinant DNA construct further comprises at least one regulatory element. In certain embodiments, the at least one regulatory element of the recombinant DNA construct comprises a promoter. In certain embodiments, the promoter is a heterologous promoter.

As used herein, a "recombinant DNA construct" comprises two or more operably linked DNA segments, preferably DNA segments that are not operably linked in nature (i.e., heterologous). Non-limiting examples of recombinant DNA constructs include a polynucleotide of interest operably linked to heterologous sequences, also referred to as "regulatory elements," which aid in the expression, autologous replication, and/or genomic insertion of the sequence of interest. Such regulatory elements include, for example, promoters, termination sequences, enhancers, etc., or any component of an expression cassette; a plasmid, cosmid, virus, autonomously replicating sequence, phage, or linear or circular single-stranded or double-stranded DNA or RNA nucleotide sequence; and/or sequences that encode heterologous polypeptides.

The polynucleotides described herein can be provided in expression cassettes for expression in a plant of interest or any organism of interest. The cassette can include 5' and 3' regulatory sequences operably linked to a polynucleotide. "Operably linked" is intended to mean a functional linkage between two or more elements. For, example, an operable linkage between a polynucleotide of interest and a regulatory sequence (e.g., a promoter) is a functional link that allows for expression of the polynucleotide of interest. Operably linked elements may be contiguous or non-contiguous. When used to refer to the joining of two protein coding regions, operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide to be under the transcriptional regulation of the regulatory regions. The expression cassette may additionally contain selectable marker genes.

The expression cassette can include in the 5'-3' direction of transcription, a transcriptional and translational initiation region (e.g., a promoter), a polynucleotide, and a transcriptional and translational termination region (e.g., termination region) functional in plants. The regulatory regions (e.g., promoters, transcriptional regulatory regions, and translational termination regions) and/or the polynucleotide may be native/analogous to the host cell or to each other. Alternatively, the regulatory regions and/or the polynucleotide may be heterologous to the host cell or to each other.

As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide that is from a species different from the species from which the polynucleotide was derived, or, if from the same/analogous species, one or both are substantially modified from their original form and/or genomic locus, or the promoter is not the native promoter for the operably linked polynucleotide.

The termination region may be native with the transcriptional initiation region, with the plant host, or may be derived from another source (i.e., foreign or heterologous) than the promoter, the polynucleotide, the plant host, or any combination thereof.

The expression cassette may additionally contain a 5' leader sequences. Such leader sequences can act to enhance translation. Translation leaders are known in the art and include viral translational leader sequences.

In preparing the expression cassette, the various DNA fragments may be manipulated, to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

As used herein "promoter" refers to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses and bacteria which comprise genes expressed in plant cells such *Agrobacterium* or *Rhizobium*. Certain types of promoters preferentially initiate transcription in certain tissues, such as leaves, roots, seeds, fibers, xylem vessels, tracheids or sclerenchyma. Such promoters are referred to as "tissue preferred." A "cell type" specific promoter primarily drives expression in certain cell types in one or more organs, for example, vascular cells in roots or leaves. An "inducible" or "regulatable" promoter is a promoter, which is under environmental control. Examples of environmental conditions that may affect transcription by inducible promoters include anaerobic conditions or the presence of light. Another type of promoter is a developmentally regulated promoter, for example, a promoter that drives expression during pollen development. Tissue preferred, cell type specific, developmentally regulated and inducible promoters constitute the class of "non-constitutive" promoters. A "constitutive" promoter is a promoter, which is active under most environmental conditions. Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (1992) Plant Mol. Biol. 18:675-689); pEMU (Last et al. (1991) Theor. Appl. Genet. 81:581-588); MAS (Velten et al. (1984) EMBO J. 3:2723-2730); ALS promoter (U.S. Pat. No. 5,659,026); ZmGOS2 (U.S. Pat. No. 6,504,083), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611. Also contemplated are synthetic promoters which include a combination of one or more heterologous regulatory elements.

C. Plants and Plant Cells

Provided are plants, plant cells, plant parts, seed, and grain comprising a polynucleotide sequence described herein or a recombinant DNA construct described herein, so that the plants, plant cells, plant parts, seed, and/or grain have increased expression of a polypeptide. In certain embodiments, the plants, plant cells, plant parts, seeds, and/or grain have stably incorporated an exogenous polynucleotide described herein into its genome. In certain embodiments, the plants, plant cells, plant parts, seeds, and/or grain can comprise multiple polynucleotides (i.e., at least 1, 2, 3, 4, 5, 6 or more).

In specific embodiments, the polynucleotide(s) in the plants, plant cells, plant parts, seeds, and/or grain are operably linked to a heterologous regulatory element, such as, but not limited to, a constitutive promoter, a tissue-preferred promoter, or a synthetic promoter for expression in plants or a constitutive enhancer. For example, in certain embodiments the heterologous regulatory element is the maize GOS2 promoter.

Also provided herein are plants, plant cells, plant parts, seeds, and grain comprising an introduced genetic modification at a genomic locus that encodes a polypeptide comprising an amino acid sequence that is at least 80% identical to an amino acid sequence selected from the group consisting of SEQ ID NOS: 1-4.

In certain embodiments, the genetic modification increases the activity of the protein. In certain embodiments, the genetic modification increases the level of the protein. In certain embodiments, the genetic modification increases both the level and activity of the protein.

A "genomic locus" as used herein, generally refers to the location on a chromosome of the plant where a gene, such as a polynucleotide encoding a polypeptide, is found. As used herein, "gene" includes a nucleic acid fragment that expresses a functional molecule such as, but not limited to, a specific protein coding sequence and regulatory elements, such as those preceding (5' non-coding sequences) and following (3' non-coding sequences) the coding sequence.

A "regulatory element" generally refers to a transcriptional regulatory element involved in regulating the transcription of a nucleic acid molecule such as a gene or a target gene. The regulatory element is a nucleic acid and may include a promoter, an enhancer, an intron, a 5'-untranslated region (5'-UTR, also known as a leader sequence), or a 3'-UTR or a combination thereof. A regulatory element may act in "cis" or "trans", and generally it acts in "cis", i.e. it activates expression of genes located on the same nucleic acid molecule, e.g. a chromosome, where the regulatory element is located.

An "enhancer" element is any nucleic acid molecule that increases transcription of a nucleic acid molecule when functionally linked to a promoter regardless of its relative position.

A "repressor" (also sometimes called herein silencer) is defined as any nucleic acid molecule which inhibits the transcription when functionally linked to a promoter regardless of relative position.

The term "cis-element" generally refers to transcriptional regulatory element that affects or modulates expression of an operably linked transcribable polynucleotide, where the transcribable polynucleotide is present in the same DNA sequence. A cis-element may function to bind transcription factors, which are trans-acting polypeptides that regulate transcription.

An "intron" is an intervening sequence in a gene that is transcribed into RNA but is then excised in the process of generating the mature mRNA. The term is also used for the excised RNA sequences. An "exon" is a portion of the sequence of a gene that is transcribed and is found in the mature messenger RNA derived from the gene but is not necessarily a part of the sequence that encodes the final gene product.

The 5' untranslated region (5'UTR) (also known as a translational leader sequence or leader RNA) is the region of an mRNA that is directly upstream from the initiation codon. This region is involved in the regulation of translation of a transcript by differing mechanisms in viruses, prokaryotes and eukaryotes.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"Genetic modification," "DNA modification," and the like refers to a site-specific modification that alters or changes the nucleotide sequence at a specific genomic locus of the plant. The genetic modification of the compositions and methods described herein may be any modification known in the art such as, for example, insertion, deletion, single nucleotide polymorphism (SNP), and or a polynucleotide modification. Additionally, the targeted DNA modification in the genomic locus may be located anywhere in the genomic locus, such as, for example, a coding region of the encoded polypeptide (e.g., exon), a non-coding region (e.g., intron), a regulatory element, or untranslated region.

As used herein, a "targeted" genetic modification or "targeted" DNA modification, refers to the direct manipulation of an organism's genes. The targeted modification may be introduced using any technique known in the art, such as, for example, plant breeding, genome editing, or single locus conversion.

The type and location of the DNA modification of the polynucleotide is not particularly limited so long as the DNA modification results in increased expression and/or activity of the protein encoded by the corresponding polynucleotide.

In certain embodiments, the plant, plant cells, plant parts, seeds, and/or grain comprise one or more nucleotide modifications present within (a) the coding region; (b) non-coding region; (c) regulatory sequence; (d) untranslated region, or (e) any combination of (a)-(d) of an endogenous polynucleotide encoding a polypeptide.

In certain embodiments the DNA modification is an insertion of one or more nucleotides, preferably contiguous, in the genomic locus. For example, the insertion of an expression modulating element (EME), such as an EME described in PCT/US2018/025446, in operable linkage with the gene of interest described herein. In certain embodiments, the targeted DNA modification may be the replacement of an endogenous promoter with another promoter known in the art to have higher expression, such as, for example, the maize GOS2 promoter. In certain embodiments, the targeted DNA modification may be the insertion of a promoter known in the art to have higher expression, such as, for example, the maize GOS2 promoter, into the 5'UTR so that expression of the endogenous polypeptide is controlled by the inserted promoter. In certain embodiments, the DNA modification is a modification to optimize Kozak context to increase expression. In certain embodiments, the DNA modification is a polynucleotide modification or SNP at a site that regulates the stability of the expressed protein.

As used herein "increased," "increase," or the like refers to any detectable increase in an experimental group (e.g., plant with a DNA modification described herein) as compared to a control group (e.g., wild-type plant that does not comprise the DNA modification). Accordingly, increased expression of a protein comprises any detectable increase in the total level of the protein in a sample and can be determined using routine methods in the art such as, for example, Western blotting and ELISA.

In certain embodiments, the genomic locus has more than one (e.g., 2, 3, 4, 5, 6, 7, 8, 9, or 10) DNA modification. For example, the translated region and a regulatory element of a genomic locus may each comprise a targeted DNA modification. In certain embodiments, more than one genomic locus of the plant may comprise a DNA modification.

The DNA modification of the genomic locus may be done using any genome modification technique known in the art or described herein. In certain embodiments the targeted DNA modification is through a genome modification technique selected from the group consisting of a polynucleotide-guided endonuclease, CRISPR-Cas endonucleases, base editing deaminases, zinc finger nuclease, a transcription activator-like effector nuclease (TALEN), engineered site-specific meganuclease, or Argonaute.

In certain embodiments, the genome modification may be facilitated through the induction of a double-stranded break (DSB) or single-strand break, in a defined position in the genome near the desired alteration. DSBs can be induced using any DSB-inducing agent available, including, but not limited to, TALENs, meganucleases, zinc finger nucleases, Cas9-gRNA systems (based on bacterial CRISPR-Cas systems), guided cpf1 endonuclease systems, and the like. In some embodiments, the introduction of a DSB can be combined with the introduction of a polynucleotide modification template.

The polynucleotides or recombinant DNA constructs disclosed herein may be used for transformation of any plant species, including, but not limited to, monocots and dicots. Additionally, the genetic modifications described herein may be used to modify any plant species, including, but not limited to, monocots and dicots.

In specific embodiments, plants of the present disclosure are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include, for example, grain plants that provide seeds of interest, oil-seed plants, and leguminous plants. Seeds of interest include, for example, grain seeds, such as corn, wheat, barley, rice, sorghum, rye, etc. Oil-seed plants include, for example, cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea.

For example, in certain embodiments, maize plants are provided that comprise, in their genome, a recombinant DNA construct comprising a polynucleotide that encodes a polypeptide comprising an amino acid sequence that is at least 80% identical to any one of SEQ ID NOS: 1-4. In certain embodiments, the polypeptide comprising an amino acid sequence that is at least 80% identical to the amino acid sequence of any one of SEQ ID NOS: 1-4. In certain embodiments, the polypeptide comprising an amino acid sequence that is at least 80% identical to the amino acid sequence of any one of SEQ ID NOS: 1-4.

In other embodiments, maize plants are provided that comprise a genetic modification at a genomic locus that encodes a polypeptide comprising an amino acid sequence that is at least 80% identical to the amino acid sequence of any one of SEQ ID NOS: 1-4. In certain embodiments, the polypeptide comprising an amino acid sequence that is at least 80% identical to the amino acid sequence of any one of SEQ ID NOS: 1-4. In certain embodiments, the polypeptide comprising an amino acid sequence that is at least 80% identical to the amino acid sequence of any one of SEQ ID NOS: 1-4.

D. Stacking Other Traits of Interest

In some embodiments, the polynucleotides disclosed herein are engineered into a molecular stack. Thus, the various host cells, plants, plant cells, plant parts, seeds, and/or grain disclosed herein can further comprise one or more traits of interest. In certain embodiments, the host cell, plant, plant part, plant cell, seed, and/or grain is stacked with any combination of polynucleotide sequences of interest in order to create plants with a desired combination of traits. As used herein, the term "stacked" refers to having multiple traits present in the same plant or organism of interest. For example, "stacked traits" may comprise a molecular stack where the sequences are physically adjacent to each other. A trait, as used herein, refers to the phenotype derived from a particular sequence or groups of sequences. In one embodiment, the molecular stack comprises at least one polynucleotide that confers tolerance to glyphosate. Polynucleotides that confer glyphosate tolerance are known in the art.

In certain embodiments, the molecular stack comprises at least one polynucleotide that confers tolerance to glyphosate and at least one additional polynucleotide that confers tolerance to a second herbicide.

In certain embodiments, the plant, plant cell, seed, and/or grain having an inventive polynucleotide sequence may be stacked with, for example, one or more sequences that confer tolerance to: an ALS inhibitor; an HPPD inhibitor; 2,4-D; other phenoxy auxin herbicides; aryloxyphenoxypropionate herbicides; dicamba; glufosinate herbicides; herbicides which target the protox enzyme (also referred to as "protox inhibitors").

The plant, plant cell, plant part, seed, and/or grain having an inventive polynucleotide sequence can also be combined with at least one other trait to produce plants that further comprise a variety of desired trait combinations. For instance, the plant, plant cell, plant part, seed, and/or grain having an inventive polynucleotide sequence may be stacked with polynucleotides encoding polypeptides having pesticidal and/or insecticidal activity, or a plant, plant cell, plant part, seed, and/or grain having an inventive polynucleotide sequence may be combined with a plant disease resistance gene.

These stacked combinations can be created by any method including, but not limited to, breeding plants by any conventional methodology, or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference. Any plant having an inventive polynucleotide sequence disclosed herein can be used to make a food or a feed product. Such methods comprise obtaining a plant, explant, seed, plant cell, or cell comprising the polynucleotide sequence and processing the plant, explant, seed, plant cell, or cell to produce a food or feed product.

II. METHODS OF USE

A. Methods for Increasing Yield, and/or Increasing the Activity of Polynucleotides in a Plant Provided are methods for increasing yield in a plant, modifying flowering time of a plant, and/or increasing the activity of one or more polynucleotides disclosed herein in a plant comprising introducing into a plant, plant cell, plant part, seed, and/or grain a recombinant DNA construct comprising any of the inventive polynucleotides described herein, whereby the polypeptide is expressed in the plant. Also provided are methods for increasing yield in a plant, modifying flowering time of a plant, and/or increasing the activity in a plant comprising introducing a genetic modification at a genomic locus of a plant that encodes a polypeptide comprising an amino acid sequence that is at least 80%-99% or 100% identical to the amino acid sequence set for in any one of SEQ ID NOS: 1-4.

The plant for use in the inventive methods can be any plant species described herein. In certain embodiments, the plant is a grain plant, an oil-seed plant, or leguminous plant. In certain embodiments, the plant is a grain plant such as maize.

As used herein, "yield" refers to the amount of agricultural production harvested per unit of land and may include reference to bushels per acre of a crop at harvest, as adjusted for grain moisture (e.g., typically 15% for maize). Grain moisture is measured in the grain at harvest. The adjusted test weight of grain is determined to be the weight in pounds per bushel, adjusted for grain moisture level at harvest.

In certain embodiments yield is measured in plants grown under optimal growth conditions. As used herein, "optimal conditions" refers to plants that are grown under well-watered or non-drought conditions. In certain embodiments, optimal growth conditions are determined based on the yield of the wild-type control plants in the experiment. As used herein, plants are considered to be grown under optimal conditions when the wild-type plant provides at least 75% of the predicted grain yield.

As used herein, "modifying flowering time" refers to a change in the number of days or growth heat units required for a plant to flower. In certain embodiments, the flowering time of the plant is delayed upon increased expression of the polypeptide. Also contemplated are embodiments in which flowering time is decreased (i.e., less days or growth heat units required for a plant to flower) upon decreased expression of the polypeptide.

As used herein, increase in photosynthetic activity, refers to any detectable increase in the functional activity of the protein compared to a suitable control. The functional activity may be any known biological property of one or more of the polypeptides disclosed herein and includes, for example, increased formation of protein complexes, modulation of biochemical pathways, and/or increased grain yield.

Various methods can be used to introduce a sequence of interest into a plant, plant part, plant cell, seed, and/or grain. "Introducing" is intended to mean presenting to the plant, plant cell, seed, and/or grain the inventive polynucleotide or resulting polypeptide in such a manner that the sequence gains access to the interior of a cell of the plant. The methods of the disclosure do not depend on a particular method for introducing a sequence into a plant, plant cell, seed, and/or grain, only that the polynucleotide or polypeptide gains access to the interior of at least one cell of the plant.

"Stable transformation" is intended to mean that the polynucleotide introduced into a plant integrates into the genome of the plant of interest and is capable of being inherited by the progeny thereof "Transient transformation" is intended to mean that a polynucleotide is introduced into the plant of interest and does not integrate into the genome of the plant or organism or a polypeptide is introduced into a plant or organism.

Transformation protocols as well as protocols for introducing polypeptides or polynucleotide sequences into plants may vary depending on the type of plant or plant cell, i.e., monocot or dicot, targeted for transformation.

In specific embodiments, the polynucleotide sequences disclosed herein can be provided to a plant using a variety of transient transformation methods. Such transient transformation methods include, but are not limited to, the introduction of the encoded protein directly into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107: 775-784, all of which are herein incorporated by reference.

In other embodiments, the inventive polynucleotides disclosed herein may be introduced into plants by contacting plants with a virus or viral nucleic acids. Generally, such methods involve incorporating a nucleotide construct of the disclosure within a DNA or RNA molecule. It is recognized that the inventive polynucleotide sequence may be initially synthesized as part of a viral polyprotein, which later may be processed by proteolysis in vivo or in vitro to produce the desired recombinant protein. Further, it is recognized that promoters disclosed herein also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) Molecular Biotechnology 5:209-221; herein incorporated by reference.

Various methods can be used to introduce a genetic modification at a genomic locus that encodes and polypeptide into the plant, plant part, plant cell, seed, and/or grain. In certain embodiments the targeted DNA modification is through a genome modification technique selected from the group consisting of a polynucleotide-guided endonuclease, CRISPR-Cas endonucleases, base editing deaminases, zinc finger nuclease, a transcription activator-like effector nuclease (TALEN), engineered site-specific meganuclease, or Argonaute.

In some embodiments, the genome modification may be facilitated through the induction of a double-stranded break (DSB) or single-strand break, in a defined position in the genome near the desired alteration. DSBs can be induced using any DSB-inducing agent available, including, but not limited to, TALENs, meganucleases, zinc finger nucleases, Cas9-gRNA systems (based on bacterial CRISPR-Cas systems), guided cpf1 endonuclease systems, and the like. In some embodiments, the introduction of a DSB can be combined with the introduction of a polynucleotide modification template.

A polynucleotide modification template can be introduced into a cell by any method known in the art, such as, but not limited to, transient introduction methods, transfection, electroporation, microinjection, particle mediated delivery, topical application, whiskers mediated delivery, delivery via cell-penetrating peptides, or mesoporous silica nanoparticle (MSN)-mediated direct delivery.

The polynucleotide modification template can be introduced into a cell as a single stranded polynucleotide molecule, a double stranded polynucleotide molecule, or as part of a circular DNA (vector DNA). The polynucleotide modification template can also be tethered to the guide RNA and/or the Cas endonuclease. Tethered DNAs can allow for co-localizing target and template DNA, useful in genome editing and targeted genome regulation, and can also be useful in targeting post-mitotic cells where function of endogenous HR machinery is expected to be highly diminished (Mali et al. 2013 Nature Methods Vol. 10: 957-963.) The polynucleotide modification template may be present transiently in the cell or it can be introduced via a viral replicon.

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

The process for editing a genomic sequence combining DSB and modification templates generally comprises: providing to a host cell, a DSB-inducing agent, or a nucleic acid encoding a DSB-inducing agent, that recognizes a target sequence in the chromosomal sequence and is able to induce a DSB in the genomic sequence, and at least one polynucleotide modification template comprising at least one nucleotide alteration when compared to the nucleotide sequence to be edited. The polynucleotide modification template can further comprise nucleotide sequences flanking the at least one nucleotide alteration, in which the flanking sequences are substantially homologous to the chromosomal region flanking the DSB.

The endonuclease can be provided to a cell by any method known in the art, for example, but not limited to, transient introduction methods, transfection, microinjection, and/or topical application or indirectly via recombination constructs. The endonuclease can be provided as a protein or as a guided polynucleotide complex directly to a cell or indirectly via recombination constructs. The endonuclease can be introduced into a cell transiently or can be incorporated into the genome of the host cell using any method known in the art. In the case of a CRISPR-Cas system, uptake of the endonuclease and/or the guided polynucleotide into the cell can be facilitated with a Cell Penetrating Peptide (CPP) as described in WO2016073433 published May 12, 2016.

In addition to modification by a double strand break technology, modification of one or more bases without such double strand break are achieved using base editing technology, see e.g., Gaudelli et al., (2017) Programmable base editing of A*T to G*C in genomic DNA without DNA cleavage. Nature 551(7681):464-471; Komor et al., (2016) Programmable editing of a target base in genomic DNA without double-stranded DNA cleavage, Nature 533(7603): 420-4.

These fusions contain dCas9 or Cas9 nickase and a suitable deaminase, and they can convert e.g., cytosine to uracil without inducing double-strand break of the target DNA. Uracil is then converted to thymine through DNA replication or repair. Improved base editors that have targeting flexibility and specificity are used to edit endogenous locus to create target variations and improve grain yield. Similarly, adenine base editors enable adenine to inosine change, which is then converted to guanine through repair or replication. Thus, targeted base changes i.e., C•G to T•A conversion and A•T to G•C conversion at one more locations made using appropriate site-specific base editors.

In an embodiment, base editing is a genome editing method that enables direct conversion of one base pair to another at a target genomic locus without requiring double-stranded DNA breaks (DSBs), homology-directed repair (HDR) processes, or external donor DNA templates. In an embodiment, base editors include (i) a catalytically impaired CRISPR-Cas9 mutant that are mutated such that one of their nuclease domains cannot make DSBs; (ii) a single-strand-specific cytidine/adenine deaminase that converts C to U or A to G within an appropriate nucleotide window in the single-stranded DNA bubble created by Cas9; (iii) a uracil glycosylase inhibitor (UGI) that impedes uracil excision and downstream processes that decrease base editing efficiency and product purity; and (iv) nickase activity to cleave the non-edited DNA strand, followed by cellular DNA repair processes to replace the G-containing DNA strand.

As used herein, a "genomic region" is a segment of a chromosome in the genome of a cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

TAL effector nucleases (TALEN) are a class of sequence-specific nucleases that can be used to make double-strand breaks at specific target sequences in the genome of a plant or other organism. (Miller et al. (2011) Nature Biotechnology 29:143-148).

Endonucleases are enzymes that cleave the phosphodiester bond within a polynucleotide chain. Endonucleases include restriction endonucleases, which cleave DNA at specific sites without damaging the bases, and meganucleases, also known as homing endonucleases (HEases), which like restriction endonucleases, bind and cut at a specific recognition site, however the recognition sites for meganucleases are typically longer, about 18 bp or more (patent application PCT/US12/30061, filed on Mar. 22, 2012). Meganucleases have been classified into four families based on conserved sequence motifs. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFs, introns, and inteins, respectively. One step in the recombination process involves polynucleotide cleavage at or near the recognition site. The cleaving activity can be used to produce a double-strand break. For reviews of site-specific recombinases and their recognition sites, see, Sauer (1994) Curr Op Biotechnol 5:521-7; and Sadowski (1993) FASEB 7:760-7. In some examples the recombinase is from the Integrase or Resolvase families.

Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind an 18 nucleotide recognition sequence.

Genome editing using DSB-inducing agents, such as Cas9-gRNA complexes, has been described, for example in U.S. Patent Application US 2015-0082478 A1, published on Mar. 19, 2015, WO2015/026886 A1, published on Feb. 26, 2015, WO2016007347, published on Jan. 14, 2016, and WO201625131, published on Feb. 18, 2016, all of which are incorporated by reference herein.

A guide polynucleotide/Cas endonuclease complex can cleave one or both strands of a DNA target sequence. A guide polynucleotide/Cas endonuclease complex that can cleave both strands of a DNA target sequence typically comprise a Cas protein that has all of its endonuclease domains in a functional state (e.g., wild type endonuclease domains or variants thereof retaining some or all activity in each endonuclease domain). Non-limiting examples of Cas9 nickases suitable for use herein are disclosed in U.S. Patent Appl. Publ. No. 2014/0189896, which is incorporated herein by reference.

Other Cas endonuclease systems have been described in PCT patent applications PCT/US16/32073, filed May 12, 2016 and PCT/US16/32028 filed May 12, 2016, both applications incorporated herein by reference.

The terms "target site", "target sequence", "target site sequence, "target DNA", "target locus", "genomic target site", "genomic target sequence", "genomic target locus" and "protospacer", are used interchangeably herein and refer to a polynucleotide sequence such as, but not limited to, a nucleotide sequence on a chromosome, episome, or any other DNA molecule in the genome (including chromosomal, choloroplastic, mitochondrial DNA, plasmid DNA) of a cell, at which a guide polynucleotide/Cas endonuclease complex can recognize, bind to, and optionally nick or cleave. The target site can be an endogenous site in the genome of a cell, or alternatively, the target site can be heterologous to the cell and thereby not be naturally occurring in the genome of the cell, or the target site can be found in a heterologous genomic location compared to where it occurs in nature. As used herein, terms "endogenous target sequence" and "native target sequence" are used interchangeable herein to refer to a target sequence that is endogenous or native to the genome of a cell and is at the endogenous or native position of that target sequence in the genome of the cell. Cells include, but are not limited to, human, non-human, animal, bacterial, fungal, insect, yeast, non-conventional yeast, and plant cells as well as plants and seeds produced by the methods described herein. An "artificial target site" or "artificial target sequence" are used interchangeably herein and refer to a target sequence that has been introduced into the genome of a cell. Such an artificial target sequence can be identical in sequence to an endogenous or native target sequence in the genome of a cell but be located in a different position (i.e., a non-endogenous or non-native position) in the genome of a cell.

An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Methods for "modifying a target site" and "altering a target site" are used interchangeably herein and refer to methods for producing an altered target site.

The length of the target DNA sequence (target site) can vary, and includes, for example, target sites that are at least 12, 13, 14, 15, 16, 17, 18, 19, 20, 21, 22, 23, 24, 25, 26, 27, 28, 29, 30 or more nucleotides in length. It is further possible that the target site can be palindromic, that is, the sequence on one strand reads the same in the opposite direction on the complementary strand. The nick/cleavage site can be within the target sequence or the nick/cleavage site could be outside of the target sequence. In another variation, the cleavage could occur at nucleotide positions immediately opposite each other to produce a blunt end cut or, in other Cases, the incisions could be staggered to produce single-stranded overhangs, also called "sticky ends", which can be either 5' overhangs, or 3' overhangs. Active variants of genomic target sites can also be used. Such active variants can comprise at least 65%, 70%, 75%, 80%, 85%, 90%, 91%, 92%, 93%, 94%, 95%, 96%, 97%, 98%, 99% or more sequence identity to the given target site, wherein the active variants retain biological activity and hence are capable of being recognized and cleaved by an Cas endonuclease. Assays to measure the single or double-strand break of a target site by an endonuclease are known in the art and generally measure the overall activity and specificity of the agent on DNA substrates containing recognition sites.

A "protospacer adjacent motif" (PAM) herein refers to a short nucleotide sequence adjacent to a target sequence (protospacer) that is recognized (targeted) by a guide polynucleotide/Cas endonuclease system described herein. The Cas endonuclease may not successfully recognize a target DNA sequence if the target DNA sequence is not followed by a PAM sequence. The sequence and length of a PAM herein can differ depending on the Cas protein or Cas protein complex used. The PAM sequence can be of any length but is typically 1, 2, 3, 4, 5, 6, 7, 8, 9, 10, 11, 12, 13, 14, 15, 16, 17, 18, 19 or 20 nucleotides long.

The terms "targeting", "gene targeting" and "DNA targeting" are used interchangeably herein. DNA targeting herein may be the specific introduction of a knock-out, edit, or knock-in at a particular DNA sequence, such as in a chromosome or plasmid of a cell. In general, DNA targeting can be performed herein by cleaving one or both strands at a specific DNA sequence in a cell with an endonuclease associated with a suitable polynucleotide component. Such DNA cleavage, if a double-strand break (DSB), can prompt NHEJ or HDR processes which can lead to modifications at the target site.

A targeting method herein can be performed in such a way that two or more DNA target sites are targeted in the method, for example. Such a method can optionally be characterized as a multiplex method. Two, three, four, five, six, seven, eight, nine, ten, or more target sites can be targeted at the same time in certain embodiments. A multiplex method is typically performed by a targeting method herein in which multiple different RNA components are provided, each designed to guide polynucleotide/Cas endonuclease complex to a unique DNA target site.

The terms "knock-out", "gene knock-out" and "genetic knock-out" are used interchangeably herein. A knock-out represents a DNA sequence of a cell that has been rendered partially or completely inoperative by targeting with a Cas protein; such a DNA sequence prior to knock-out could have encoded an amino acid sequence, or could have had a regulatory function (e.g., promoter), for example. A knock-out may be produced by an indel (insertion or deletion of nucleotide bases in a target DNA sequence through NHEJ), or by specific removal of sequence that reduces or completely destroys the function of sequence at or near the targeting site.

The guide polynucleotide/Cas endonuclease system can be used in combination with a co-delivered polynucleotide modification template to allow for editing (modification) of a genomic nucleotide sequence of interest. (See also U.S. Patent Application US 2015-0082478 A1, published on Mar. 19, 2015 and WO2015/026886 A1, published on Feb. 26, 2015, both are hereby incorporated in its entirety by reference.)

The terms "knock-in", "gene knock-in, "gene insertion" and "genetic knock-in" are used interchangeably herein. A knock-in represents the replacement or insertion of a DNA sequence at a specific DNA sequence in cell by targeting with a Cas protein (by HR, wherein a suitable donor DNA polynucleotide is also used). Examples of knock-ins are a specific insertion of a heterologous amino acid coding sequence in a coding region of a gene, or a specific insertion of a transcriptional regulatory element in a genetic locus.

The following are examples of specific embodiments of some aspects of the invention. The examples are offered for illustrative purposes only and are not intended to limit the scope of the invention in any way.

Example 1

Expression of Endogenous Transcription Factor by Promoter Insertion or Replacement This example demonstrates that expression of an endogenous maize MADS transcription factor ZmM28 (SEQ ID NO: 1) is modulated by a heterologous promoter element. In an embodiment, heterologous ZmGOS2 promoter from maize is used to replace an endogenous regulatory region of the genomic locus that encodes SEQ ID NO: 1 polypeptide or a sequence that is substantially similar to SEQ ID NO: 1. The heterologous regulatory elements (e.g., promoters and introns) were replaced by targeted site-specific homologous recombination. For example, guide RNAs were designed to target the upstream regulatory regions of the genomic locus that drives the expression of the polynucleotide encoding SEQ ID NO: 1. A schematic illustration is provided in FIG. 1.

In an embodiment, Cas9 genome editing technique was used to replace the endogenous promoter region of the genomic loci that encodes SEQ ID NO: 1 with promoters to increase one or more agronomic parameters. For one such approach, a moderatively-constitutive promoter promoter (ZM-GOS2) was used to replace the endogenous promoter. In another embodiment, a different moderately expressed constitutive promoter, OS-ACTIN was used to replace the endogenous promoter. Therefore, by modulating the expression of the polynucleotide that encodes SEQ ID NO: 1 through targeted genome editing approach, agronomic parameters can be evaluated.

The process of screening the T0 events and the subsequent T1 plants for Cas9 gene editing of SEQ ID NO:1 encoding gene is summarized herein. These approaches included a promoter insertion, two different promoter replacements and deletion (CR4-CR11) knockouts generated via the promoter replacement attempts.

T0 plants were generated using particle gun bombardment through co-bombardment of the insert plasmid, Cas9 plasmid, gRNA plasmid(s) and three helper plasmids. Genomic DNA was isolated from the T0 plants and copy number analysis of plasmids were performed. HR1 and HR2 junction PCRs were performed to select the T0s for further evaluation. A subsequent, more detailed screening was done in which long-range PCRs (HR1 & HR2 PCRs) was performed to cover the expanse of the intended insertion region as well as some anchoring native flanking region on each side. Based on the HR1 & HR2 PCR product sizes combined with the support lab's copy number information, events were selected for embryo rescue (to shorten the time between generations) to continue to the T1 generation.

Once T1 plants were in flats they were sampled at a young stage for genomic DNA isolation and the copy number analysis was performed again checking for all plasmids and then HR1 and HR2 long PCRs were performed checking for the correct size. Using combined information, five to ten plants per event were selected for transplant. HR1 & HR2 PCRs from those selected T1 plants were cloned and sequenced. Tissue was also collected from the plants to submit for SBS and for another support lab to develop genotyping and copy number assays for the intended modification.

After HR1/HR2 fragment sequencing and SBS analysis on the T1s, events that had perfect replacements were not identified for the promoter insertion or promoter replacements. A few events had the CR4-CR11 region deleted and came back SBS clean. In addition, an alternate null allele was identified that resulted from a one base pair insertion that caused a frameshift at the CR11 site.

TABLE 2

| Genome editing approaches for gRNA design | |
|---|---|
| Guide RNA target sites | Design Approach |
| CR24 (SEQ ID NO: 19) + CR1 (SEQ ID NO: 21) | Replace endogenous ZM-ZMM28 promoter with ZM-GOS2 PRO:ZM-UBI INTRON1 |
| CR4 (SEQ ID NO: 16) + CR10 (SEQ ID NO: 14) | Replace endogenous ZM-ZMM28 promoter with ZM-GOS2 PRO:ZM-UBI INTRON1 |

Several designs were considered for removing and replacing the endogenous promoter regions and some of those designs are shown in Table 2. For example, Design 1 included: ZM-ZMM28-CR4//ZM-ZMM28-CR10 (981 bp); ZM-GOS2 PRO:UBI1ZM INTRON1 (1912 bp) and Design 2 included ZM-ZMM28-CR24//ZM-ZMM28-CR1 (1066 bp); ZM-GOS2 PRO:UBI1ZM INTRON1 (1914 bp) as shown in FIG. 1.

Figure 2:
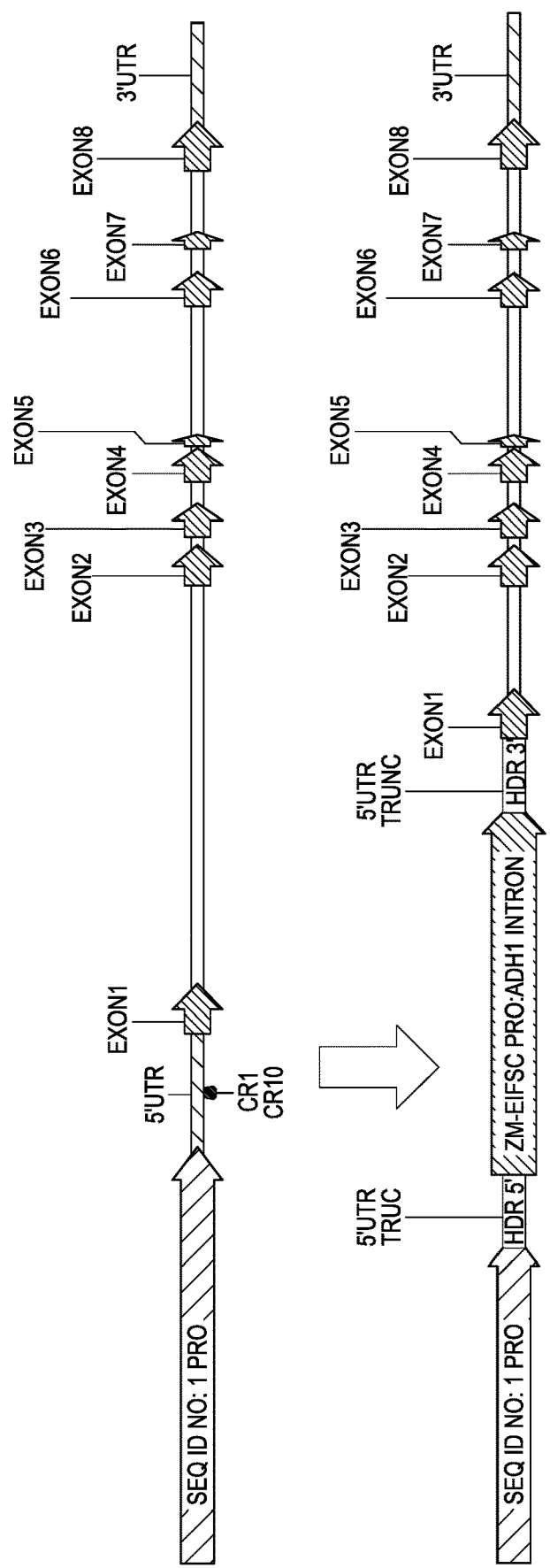

In another embodiment, Zm-EIFC promoter+ADH1 intron is inserted into the locus of the polynucleotide encoding SEQ ID NO: 1. For example, as shown in FIG. 2, CR1 and CR10 recognition regions for Cas-endonuclease mediated double strand break, are used to insert ZM-ZMM28-CR1-Insert ZM-EIF5C PRO:ADH1 INTRON into native ZM-ZMM28 5'UTR (2112 bp) and in another approach, ZM-ZMM28-CR10-Insert ZM-EIF5C PRO:ADH1 INTRON into native ZM-ZMM28 5'UTR (2112 bp).

Other examples for promoter replacement or insertion include UBI1ZM PRO:ADH1 INTRON1 as a replacement, ZM-H1B PRO (1.2 KB)(MOD1):ADH1 INTRON1 as a replacement and ZM-H1B PRO (1.2 KB)(MOD1):ADH1 INTRON1 as an insertion.

Therefore, this Example demonstrates that heterologous promoters can be inserted and/or replaced with the endogenous promoter region of the genomic locus that encodes SEQ ID NO: 1.

Example 2

Figure 4:
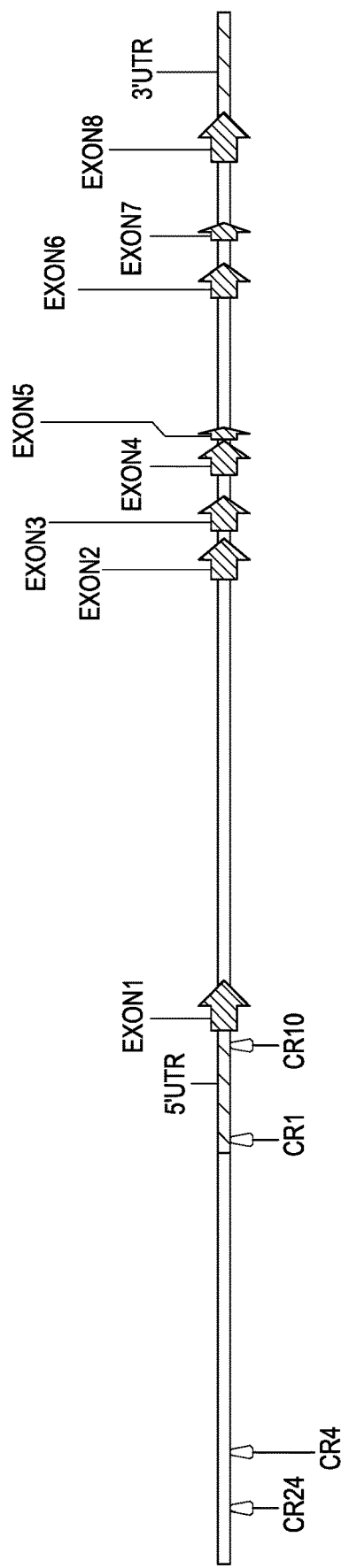
FIG. 4 is a schematic illustration showing additional CRISPR recognition sites for promoter alteration.

Expression of Endogenous Transcription Factor by Insertion and/or Creation of Heterologous Expression Modulating Elements Modulating expression of endogenous maize MADS28 through one or more heterologous enhancer element in maize enhances grain yield. Upstream promoter and/or untranslated regions of zmm28 gene are shown in FIG. 4. Enhancer elements such as those described for example in Table 1 of WO2018183878A1, incorporated herein by reference. Suitable expression modulating elements (EME) include for example one or more copies (1×-4×) of SEQ ID NOS: 1-10 from Table 1 of WO2018183878A1.

Based on the upstream regulatory region of the genomic locus containing zmm28 gene, EME sequences can be inserted as discrete heterologous sequences or the regulatory region can be genome edited (either using a template directed double strand-break repair or through base editing deaminases) to create heterologous enhancer sequences that modulate the expression level of zmm28.

Incorporation of the EMEs are done by a variety of different ways including targeted insertion of one or more copies of the EMEs and/or in combination with creating one or more copy of the EMEs in the promoter regions of the endogenous locus of zmm28. For example, at about 10-100 bp upstream from the transcriptional start site (TSS), one or more copies of the EMEs can be inserted through homologous recombination or by base editing or template-driven repair. Inclusion of the EMEs at suitable regions of zmm28 locus results in increased and extended expression of the polynucleotide encoding SEQ ID NO: 1 or 2.

TABLE 3

Effect of heterologous maize-derived enhancer elements in modulating gene expression in the regulatory region of the genomic loci encoding SEQ ID NO: 1 in protoplasts.

| Description | Location (from TATA (bp)) | Expression modulating element (EME) | Harmonic Mean | Standard Dev | Sample Size |
|---|---|---|---|---|---|
| ZM-GOS2 PRO (positive control) | | None | 1.20 | 1.60 | 1922 |
| UBI1ZM PRO (positive control) | | None | 3.53 | 7.90 | 2035 |
| ZM-ADF4 PRO (positive control) | | None | 0.27 | 0.15 | 1287 |
| ZMM28 PRO (control) | | None (control) | 0.04 | 0.05 | 2513 |
| ZMM28 PRO | −92 | ZM-AS2 (16 bp) | 0.29 | 0.28 | 2241 |
| ZMM28 PRO | −21 | ZM-AS2 (16 bp) | 1.26 | 1.36 | 2683 |
| ZMM28 PRO | −21 & −92 | 2X ZM-AS2 (16 bp) | 1.67 | 1.71 | 2703 |
| ZMM28 PRO | −21 | ZM-AS2 (16bp) + TATA (Optimized) | 2.03 | 2.16 | 2325 |
| ZMM28 PRO | −21 | Null (16 bp) (negative control) | 0.09 | 0.13 | 2109 |
| Second Protoplast Source | | | | | |
| ZM-GOS2 PRO (positive control) | | None | 1.45 | 1.92 | 2315 |
| UBI1ZM PRO (positive control) | | None | 4.55 | 8.83 | 964 |
| ZM-ADF4 PRO (positive control) | | None | 0.23 | 0.15 | 1146 |
| ZMM28 PRO (control) | | None (control) | 0.03 | 0.03 | 973 |
| ZMM28 PRO | −92 | ZM-AS2 (16 bp) | 0.22 | 0.17 | 561 |
| ZMM28 PRO | −21 | ZM-AS2 (16 bp) | 1.30 | 1.11 | 846 |
| ZMM28 PRO | −21 & −92 | 2X ZM-AS2 (16 bp) | 2.12 | 1.57 | 539 |
| ZMM28 PRO | −21 | ZM-AS2 (16 bp) + TATA(Opt) | 2.24 | 2.22 | 1045 |
| ZMM28 PRO | −21 | Null (16 bp) (negative control) | 0.07 | 0.14 | 175 |

As shown in the table above, presence of a heterologous maize-derived expression modulating element (e.g., SEQ ID NO: 23) in the promoter region of Zmm28 gene increases expression in the test system. For example, two copies of the Zm-AS2 EME increases expression level when the EME is present in the regions of about −21 bp and −92 bp as measured from TATA. Further, one copy of the EME when present in the −21 bp region from TATA increases gene expression (marker gene) in the maize protoplast system to a higher level than the same EME when present about −92 bp from the TATA box. The various embodiments of the EME within the promoter regions of Zmm28 gene are shown in SEQ ID NOS: 24-28. These changes are readily made in the endogenous genomic regions of the Zmm28 gene through site-directed genome editing—e.g., Cas endonuclease and/or base editing using one or more deaminases.

Figure 5:
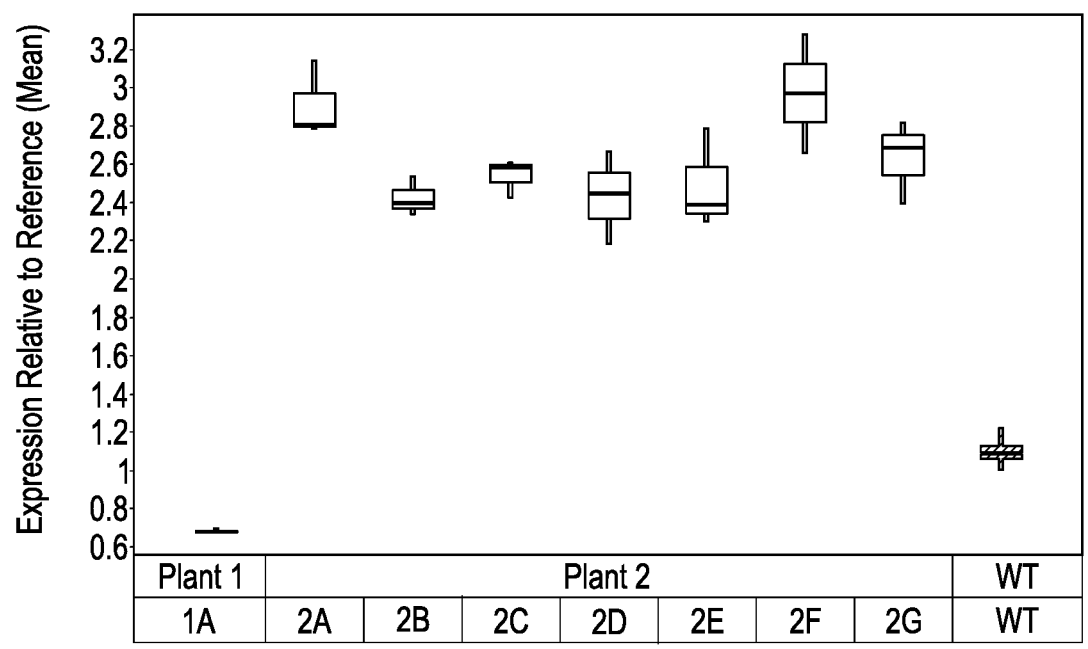
FIG. 5 shows expression levels in maize plants that were genome edited with expression modulation elements.

Maize plants were successfully created using genome editing by a template directed double strand-break repair in the genomic locus encoding SEQ ID NO: 1. Maize plants were identified that had one copy of 22 bp maize EME (SEQ ID NO: 3 as described in WO2018183878A1, incorporated herein by reference) inserted at −21 of TATA, while another maize plant was identified that had 7 bp changed in the native promoter to create one copy of 16 bp maize EME (SEQ ID NO: 4 as described in WO2018183878A1) 21 nucleotides upstream of TATA. Thus, one copy of the EME was added to the native promoter in both of these maize plants. However, in one case, an additional sequence was added to the native promoter while in the other plant the native promoter sequence was altered without changing the size of this region of the promoter. The maize plants in which the EME sequence was created by altering the native sequence had a 2.2 to 2.7-fold increase in mRNA (encoding SEQ ID NO: 1), expression when compared to a wild-type plant with only the native regulatory sequence (FIG. 5).

Figure 6:
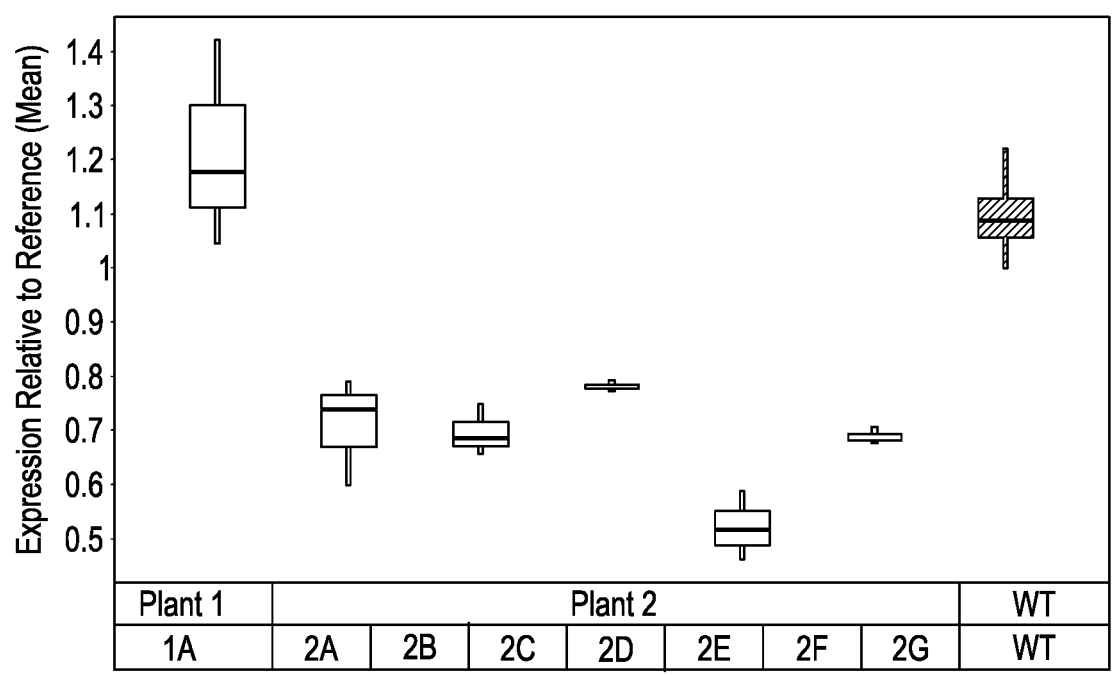
FIG. 6 shows expression levels in maize plants where expression modulation elements were inserted into the endogenous regulatory region.

Three or four samples were taken from the uppermost expanded leaf of each plant at the VT developmental stage and evaluated for RNA expression. Plant 1 and Plant 2 are independently derived plants that had the desired change by inserting one copy of the EME in Zmm28 promoter region. Wild-type (WT) plant had 1.4 to 2.1-fold higher expression than the progeny of Plant 2 (listed as 2A-2E). The one plant, which shows a similar expression level of WT, is the progeny of Plant 1. Plant 1A had an undesired change to the sequence within Zmm28 locus and showed lower RNA expression than wild-type (WT). The progeny of plant 2 (listed as 2A-2G), which had the desired edit creating one copy of the EME, showed a 2.2 to 2.7-fold increase in RNA expression when compared to WT. Maize plants with the EME sequence inserted in the native regulatory region of Zmm28 locus promoter did not result in a significant increase in the mRNA expression of the endogenous gene. The progeny from one plant (Plant 2A-2E in FIG. 6) with this desired change showed a reduction in RNA expression while the progeny (Plant 1A in FIG. 6) from a second independent plant with the desired edit exhibited RNA expression level similar to the level detected in wild-type plants (FIG. 6). Another maize plant had two copies of a 27 bp sequence inserted at −53 of TATA sequence. This 27 bp sequence includes the 22 bp EME sequence (SEQ ID NO: 3 as described in WO2018183878A1). Transient data for 2 copies of this EME sequence inserted in Zmm28 promoter exhibited a 4.88-fold increase in normalized fluorescence expression when compared to the native promoter without EME.

The progeny of a maize plant with the desired edit of two copies of a 27 bp maize sequence inserted at −53 of TATA sequence as described previously, were selfed, creating a segregating population of plants homozygous, heterozygous or null for this change at the Zmm28 locus. Young seedlings were sampled for genomic DNA isolation, and then copy number analysis was performed to determine zygosity for each plant. In maize leaf tissue at V3 developmental stage, a significant increase in Zmm28 RNA expression was determined for maize plants homozygous or heterozygous for the 2×EME insertion when compared to Zmm28 mRNA expression levels in the control/nulls (Table 4). There was a significant change in Zmm28 RNA expression amongst different zygosity with the highest Zmm28 RNA expression detected in plants homozygous for the 2×EME insertion.

TABLE 4

Effect of maize-derived 2X EME insertion in Zmm28 promoter in modulating RNA gene expression in a segregating population of plants, which are homozygous for the 2X EME, heterozygous for 2X EME or null (no copies of EME) at t he Zmm28 locus. Wild-type (WT) plants in the same genetic background were also evaluated for native Zmm28 RNA expression levels.

| Zygosity | Mean | stdErr |
| --- | --- | --- |
| Heterozygous | 2.738991 | 0.050522 |
| Homozygous | 4.723187 | 0.106618 |
| NULL | 0.11896 | 0.037889 |
| WT | 0.01586 | 0.001897 |

Therefore, this Example demonstrates that heterologous expression elements engineered into the endogenous location of the genome increased expression of a maize MADS box protein, in an aspect the expression of an endogenous gene encoding SEQ ID NO: 1 or an allelic variant thereof. This increased expression of the endogenous MADS box protein in maize is expected to exhibit increase or improvement in one or more agronomic characteristics such as increased kernel set, weight or number, grain yield, and other grain-yield related secondary characteristics.

Example 3

Figure 3:
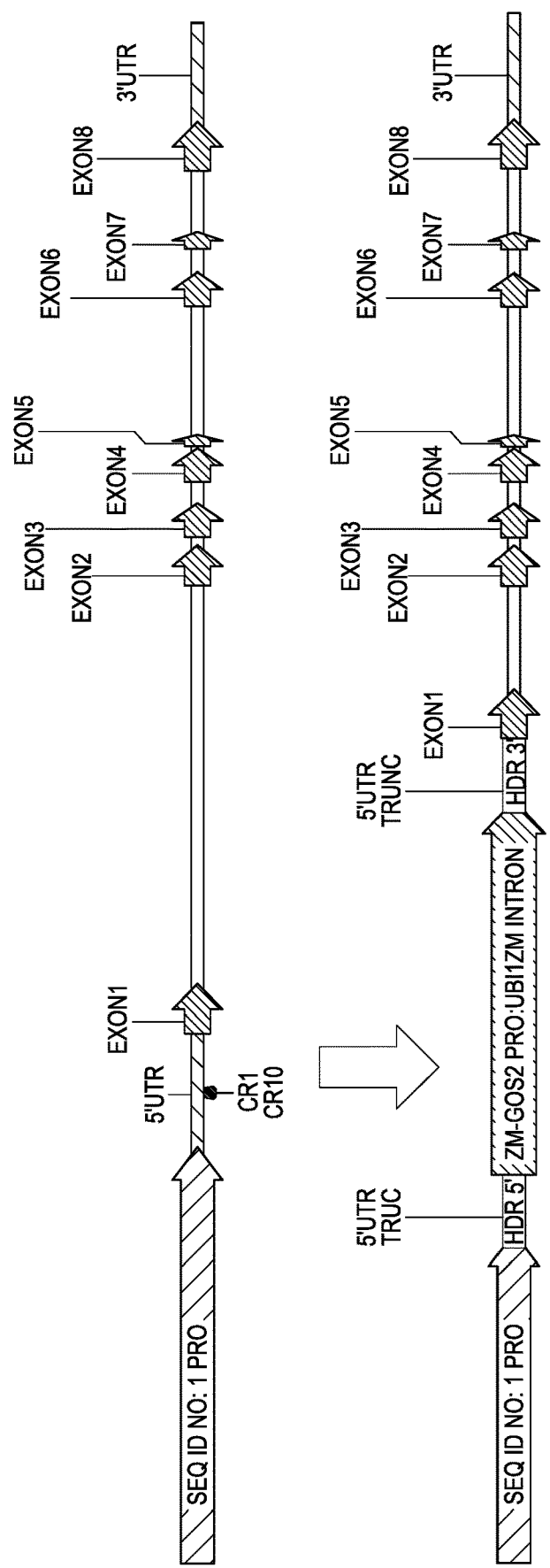

Expression of Endogenous Transcription Factor by Endogenous Promoter and/or Intron Manipulation This example demonstrates the analysis of increasing expression of endogenous MADS box proteins in maize by intron manipulation. As shown in any of FIGS. 1-3, the genomic locus encoding SEQ ID NO: 1 has introns. Compositions and methods are provided herein to edit, delete, replace one or more endogenous introns of zmm28. For example, Intron 1 of zmm28 is large and may contain (negative) regulatory elements, particularly with regards to spatial regulation. Similarly, endogenous zmm28 promoter regions are deleted to improve expression levels and/or patterns. Some of the promoter deletions are shown in Table 5A and some of the intron deletions are shown in Table 5B.

TABLE 5A

Promoter deletions.

| Promoter Deletion (proximal to distal) | Size |
| --- | --- |
| (CR8-CR9) | 201 bp |
| (CR7-CR8) | 273 bp |
| (CR6-CR7) | 197 bp |
| (CR6-CR9) | 671 bp |
| (CR6-CR8) | 470 bp |
| (CR7-CR9) | 474 bp |

TABLE 5B

Intron deletions

| Intron Deletion (5'-3") | Size |
| --- | --- |
| (CR12-CR13) | 220 bp |
| (CR13-1R14) | 192 bp |
| (CR14-CR15) | 162 bp |
| (CR15-CR16) | 260 bp |
| (CR16-CR17) | 252 bp |
| (CR17-CR18) | 226 bp |
| (CR18-CR19) | 178 bp |
| (CR19-CR20) | 183 bp |
| (CR20-CR21) | 272 bp |
| (CR21-CR22) | 433 bp |
| (CR12-CR18) | 1313 bp |
| (CR17-CR22) | 1293 bp |
| (CR12-CR22) | 2379 bp |

As shown in Tables 5A and 5B, several promoter and/or intron deletions of the endogenous zmm28 gene locus can modulate endogenous gene expression. Different promoter and/or regulatory elements modification can result in e.g., increase in expression strength (magnitude) and/or specificity (e.g., tissue preferred), which can be further evaluated for yield increase purposes and tested under various stress environments, such as drought and/or low nitrogen growing conditions.

Example 4

Polymorphisms that Regulate Gene Expression and/or Polypeptide Activity

This example demonstrates that genetic polymorphisms in the endogenous genomic locus that encodes MADS box proteins in maize by site-directed mutagenesis or screening for variations in the germplasm based on the guidance and teachings provided herein. As shown herein the polypeptide represented by SEQ ID NO: 1 has several domains including protein-protein interaction domains and protein-DNA interaction domain (e.g., transcription factor). One or more mutations or changes in the nucleotide sequence encoding SEQ ID NO: 1 can result in increased activity of a protein variant or may increase the expression level of the transcript that results in SEQ ID NO: 1. For example, The ZMM28 transcription factor is an MIKC protein which contains an N-terminal MADS domain (amino acids 1-61 of SEQ ID NO: 1) involved in DNA-binding, followed by an Intervening (I) region (amino acids 62-87 of SEQ ID NO: 1) and a Keratin-like (K) box (amino acids 88-169 of SEQ ID NO: 1) which are both involved in DNA binding and protein-protein interactions, and a C-terminal domain (amino acids 170-251 of SEQ ID NO: 1) that is involved in activity and ternary complex formation. The MIKC structure and the corresponding ZMM28 amino acid sequence is represented by SEQ ID NO: 1.

Compositions and methods are provided herein to edit, delete, replace or otherwise modify one or more nucleotides or regions or fragments of the genomic locus encoding one of SEQ ID NOs: 1-3 or an amino acid sequence that is at least 90% identical to one of those sequences. One or more of these changes modulate the binding and/or other activation characteristics to result in modulating for example, interaction partners of SEQ ID NO: 1 or direct targets of SEQ ID NO: 1 in a maize plant cell. Therefore, this Example demonstrates that by modifying one or more motifs, domains, or amino acid residues of SEQ ID NO: 1, maize grain yield can be increased compared to a maize plant not having such modifications.

Example 5

Targeted Activation of Endogenous Maize MADS Box Transcription Factor

This example demonstrates that there are several methods to direct targeted activation of the expression of the endogenous loci encoding SEQ ID NO: 1 or an amino acid sequence that is at least 90% identical to the endogenous sequence in maize. For example, one such approach includes to engineer a deactivated Cas endonuclease, such as for example, a dCas9 coupled with an activation domain (e.g., a transcription factor activation domain) whereby the dCas9 coupled with or otherwise associated with an activation domain, is guided by a guide polynucleotide to bind and activate the expression of the endogenous gene encoding SEQ ID NO: 1 or a maize homolog thereof.

In another example, an endogenous miRNA target can be edited so that the miRNA does not target its cognate sequence in the genomic region encoding the SEQ ID NO: 1 polypeptide. In another example, the endogenous miRNA target sequence present within the genomic region can be edited such that the endogenous miRNA no longer can effectively target and repress the gene expression.

Example 6

Identifying Haplotypes and Maize Germplasm Variations for Maize MADS Transcription Factors This example demonstrates that genetic variations in the genomic region of the genomic locus that encodes SEQ ID NO: 1 are identified by sequencing, marker-assisted selection, whole genome prediction or any other type of genotyping methods based on the teachings provided herein. For example, elite maize inbreds and/or hybrids are genotyped to associate genotypic variations in the genomic sequence encoding SEQ ID NO: 1 or a homolog thereof, to predict yield gain or evaluate for grain yield. This is accomplished by for example, sequencing or otherwise genotyping the genomic region that encodes the SEQ ID NO: 1 polypeptide based on the sequence information available to design and/or infer genotypic association knowledge. The variations in the genomic region in and around the loci that expresses a polypeptide similar to SEQ ID NO: 1 are identified and/or correlated with one or more observed or predicted phenotypic characteristic, e.g., yield or biomass. One or more such alleles are introgressed into a desirable background maize background. In another example, any quantitative trait loci (QTL) associations are fine-mapped using the sequence information of SEQ ID NO: 1.

These genetic variations in the germplasm for the genomic loci encoding SEQ ID NO: 1 or a polypeptide that is substantially similar to SEQ ID NO: 1 may be introduced by a traditional mutagenesis method such as for example, EMS or may be selected from naturally occurring variations. For example, targeted genome editing technologies can be used to introduce variations or specific changes in the genomic loci encoding SEQ ID NO: 1, and then traditional mutagenesis methods can be used to introduce changes, but screened based on knowledge obtained from the genome edited changes.

Terms used in the claims and specification are defined as set forth below unless otherwise specified. It must be noted that, as used in the specification and the appended claims, the singular forms "a," "an" and "the" include plural referents unless the context clearly dictates otherwise.

All publications and patent applications in this specification are indicative of the level of ordinary skill in the art to which this invention pertains. All publications and patent applications are herein incorporated by reference to the same extent as if each individual publication or patent application was specifically and individually indicated by reference.

Unless defined otherwise, all technical and scientific terms used herein have the same meaning as commonly understood by one of ordinary skill in the art to which this invention belongs. Unless mentioned otherwise, the techniques employed or contemplated herein are standard methodologies well known to one of ordinary skill in the art. The materials, methods and examples are illustrative only and not limiting.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

Units, prefixes and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

We claim:

1. A maize plant cell comprising an introduced targeted genetic modification within an endogenous gene that encodes a polypeptide comprising an amino acid sequence that is at least 98% identical to the amino acid sequence of SEQ ID NO: 4, wherein the targeted genetic modification is an insertion of a heterologous promoter or an enhancer element at the genomic locus of the endogenous gene and wherein the targeted modification results in an increased expression level of the polynucleotide encoding the polypeptide.

2. The plant cell of claim 1, wherein the targeted genetic modification is present in (a) the coding region; (b) a non-coding region; (c) a regulatory sequence; (d) an untranslated region; or (e) any combination of (a)-(d) of the gene that encodes the polypeptide.

3. The plant cell of claim 1, wherein the targeted genetic modification is introduced by a site-specific polynucleotide-guided Cas endonuclease.

4. A maize seed comprising a targeted genetic modification in an endogenous gene that encodes a polypeptide comprising an amino acid sequence that is at least 98% identical to the amino acid sequence of SEQ ID NO: 4, wherein the targeted genetic modification is an insertion of a heterologous promoter or an enhancer element at the genomic locus of the endogenous gene, and wherein the targeted modification results in increased expression level of the polynucleotide encoding the polypeptide.

5. The maize seed of claim 4, wherein the targeted genetic modification is present in (a) the coding region; (b) a non-coding region; (c) a regulatory sequence; (d) an untranslated region; or (e) any combination of (a)-(d) of the gene that encodes the polypeptide.

6. The maize seed of claim 4, wherein the seed further comprises a polypeptide conferring herbicide tolerance and/or insect resistance.

7. The maize seed of claim 4, wherein the heterologous promoter is a ZmGOS2 promoter.

8. A method of introducing a site-directed modification within a gene to increase expression level of a polynucleotide, the method comprising:
   a. introducing in a regenerable maize plant cell a targeted genetic modification in an endogenous gene that encodes a polypeptide comprising an amino acid sequence that is at least 98% identical to the amino acid sequence of SEQ ID NO: 4, wherein the modification is swapping an endogenous promoter element of the endogenous gene at the genomic locus with a heterologous regulatory element; and
   b. obtaining the maize plant, wherein the expression level of the encoded polypeptide is increased compared to a control plant.

9. The method of claim 8, wherein the heterologous regulatory element is a constitutive promoter.

10. The method of claim 8, wherein the targeted modification is in one or more of the MIKC domains of the polypeptide.

* * * * *